United States Patent
Van Haren et al.

(10) Patent No.: US 10,881,729 B2
(45) Date of Patent: Jan. 5, 2021

(54) VACCINE ADJUVANT COMPOSITIONS

(71) Applicant: CHILDREN'S MEDICAL CENTER CORPORATION, Boston, MA (US)

(72) Inventors: Simon D. Van Haren, Somerville, MA (US); Ofer Levy, Cambridge, MA (US); David J. Dowling, Brighton, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 15/305,004

(22) PCT Filed: Apr. 17, 2015

(86) PCT No.: PCT/US2015/026411
§ 371 (c)(1),
(2) Date: Oct. 18, 2016

(87) PCT Pub. No.: WO2015/161218
PCT Pub. Date: Oct. 22, 2015

(65) Prior Publication Data
US 2017/0224811 A1 Aug. 10, 2017

Related U.S. Application Data

(60) Provisional application No. 62/003,861, filed on May 28, 2014, provisional application No. 61/981,397, filed on Apr. 18, 2014.

(51) Int. Cl.
| | |
|---|---|
| *A21C 3/00* | (2006.01) |
| *A61K 39/39* | (2006.01) |
| *A61K 35/74* | (2015.01) |
| *A61K 45/06* | (2006.01) |
| *A61K 31/739* | (2006.01) |
| *A61K 31/55* | (2006.01) |
| *A61K 31/4745* | (2006.01) |
| *A61K 31/716* | (2006.01) |
| *A61K 31/7024* | (2006.01) |
| *A61K 39/112* | (2006.01) |
| *A61K 39/29* | (2006.01) |
| *C12N 7/00* | (2006.01) |
| *A61K 39/00* | (2006.01) |

(52) U.S. Cl.
CPC .......... *A61K 39/39* (2013.01); *A61K 31/4745* (2013.01); *A61K 31/55* (2013.01); *A61K 31/7024* (2013.01); *A61K 31/716* (2013.01); *A61K 31/739* (2013.01); *A61K 35/74* (2013.01); *A61K 39/0275* (2013.01); *A61K 39/29* (2013.01); *A61K 45/06* (2013.01); *C12N 7/00* (2013.01); *A61K 2039/55505* (2013.01); *A61K 2039/55511* (2013.01); *A61K 2039/55516* (2013.01); *A61K 2039/55566* (2013.01); *A61K 2039/55572* (2013.01); *A61K 2039/57* (2013.01); *C12N 2770/24234* (2013.01)

(58) Field of Classification Search
None
See application file for complete search history.

(56) References Cited

U.S. PATENT DOCUMENTS

| | | |
|---|---|---|
| 8,501,186 B2 | 8/2013 | Jadhav et al. |
| 2002/0193729 A1 | 12/2002 | Cormier et al. |
| 2011/0020386 A1 | 1/2011 | Gierahn et al. |
| 2011/0287087 A1 | 11/2011 | Christensen et al. |

OTHER PUBLICATIONS

Dowling et al. PLOS vol. 8, issue 3, pp. 1-11, Mar. 2013 (Year: 2013).*
Cambi et al., "Dual function of C-type lectin-like receptors in the immune system", Curr. Opin. Cell Biol. 15:539-546 (2003).
Cambi et al., "How C-type lectins detect pathogens", Cell. Microbiol. 7(4):481-488 (2005).
Cavicchi et al., "Franklin Pierce Law Center Educational Report: Patent Landscape of Adjuvant for HIV Vaccines", Franklin Pierce Law Center (2009). 150pp.
Dekker et al., "Dose Optimization Strategies for Vaccines: The Role of Adjuvants and New Technologies", Report Approved at NVAC Meeting Feb. (2008).
Dennehy et al., "Syk kinase is required for collaborative cytokine production induced through Dectin-1 and Toll-like receptors", Eur. J. Immunol. 38:500-506 (2008).
Dowling et al., "The Ultra-Potent and Selective TLR8 Agonist VTX-294 Activates Human Newborn and Adult Leukocytes", PLoS One 8(3):e58164 (2013).

(Continued)

*Primary Examiner* — Jana A Hines
*Assistant Examiner* — Khatol S Shanhnan Shah
(74) *Attorney, Agent, or Firm* — Nixon Peabody LLP; David S. Resnick; Ravinderjit Braich

(57) ABSTRACT

Embodiments described herein relate to combinatorial compositions and uses thereof, for example, as vaccine adjuvant compositions, for enhancing immune response, for inducing differentiation of nave T cells to differentiate into IFN-γ-producing T cells, and for preventing and treating infections. The combinatorial composition comprises TLR and CLR agonists. The combinatorial composition comprises at least one TLR4 agonist and at least one Dectin-1 agonist, wherein the at least TLR4 agonist is monophosphoryl lipid A (MPLA) or glycopyranosyl lipid A (GLA), or the combinatorial composition comprises at least one TLR7/8 agonist and at least one Mincle agonist.

16 Claims, 9 Drawing Sheets
Specification includes a Sequence Listing.

(56) References Cited

OTHER PUBLICATIONS

Eberle et al., "Dectin-1 Stimulation Induces Suppressor of Cytokine Signaling 1, Thereby Modulating TLR Signaling and T Cell Responses", J. Immunol. 188:5644-5654 (2012).

Foppen et al., "In Vitro Modeling of Neonatal Dendritic Cells Identifies Distinct Synergy Between Toll-Like Receptor and C-Type Lectin Receptor Agonists", PAS Meeting Abstract May 5, 2014.

Gantner et al., "Collaborative Induction of Inflammatory Responses by Dectin-1 and Toll-like Receptor 2", J. Exp. Med. 197(9):1107-1117 (2003).

Geijtenbeek et al., "Signalling through C-type lectin receptors: shaping immune responses", Nat. Rev. Immunol. 9:465-479 (2009).

InvivoGen, "TLR7 and TLR8: Key players in the antiviral response", InvivoGen Insight (2006).

Kingeter et al., "C-type lectin receptor-induced NF-κB activation in innate immune and inflammatory responses", Cell. Mol. Immunol. 9:105-112 (2012).

Lee et al., "Neutrophils Promote Mycobacterial Trehalose Dimycolate-Induced Lung Inflammation via the Mincle Pathway", PLoS Pathog. 8(4):e1002614 (2012).

Sousa et al., "Restoration of Pattern Recognition Receptor Costimulation to Treat Chromoblastomycosis, a Chronic Fungal Infection of the Skin", Cell Host & Microbe 9:436-443 (2011).

Van Haren et al., "An in vitro screen employing human neonatal dendritic cells identifies distinct synergy between Toll-like receptor and C-type lectin receptor agonists (VAC10P.966)", J. Immunol. 192(1 Supplement):204.5 (2014). (Abstract).

Data Sheet: CL097: Imidazoquinoline Compound—TLR 7/8 ligand, Version #12F13-MM. InvivoGen, http://www.invivogen.com/PDF/CL097_TDS.pdf. Accessed Oct. 14, 2016.

Ferwerda et al., "Dectin-1 synergizes with TLR2 and TLR4 for cytokine production in human primary monocytes and macrophages." Cellular Microbiology 10(10):2058-2066 (2008).

Ferwerda et al., "The role of Toll-like receptors and C-type lectins for vaccination against Candida albicans." Vaccine 28(3):614-622 (2010).

Seo et al., "Dectin-1 stimulation selectively reinforces LPS-driven IgG1 production by mouse B cells." Immune Network 13(5):205-212 (2013).

\* cited by examiner

VACCINE ADJUVANT COMPOSITIONS

CROSS REFERENCE TO RELATED APPLICATION

This application is a 35 U.S.C. § 371 National Stage entry application of the International Application No. PCT/US2015/026411 filed on Apr. 17, 2015, which designates the United States and which claims the benefit under 35 U.S.C. § 119(e) of the U.S. Provisional Application No. 61/981,397 filed on Apr. 18, 2014 and the U.S. Provisional Application No. 62/003,861 filed on May 28, 2014, the contents of each application are incorporated herein by reference in its their entireties.

SEQUENCE LISTING

The instant application contains a Sequence Listing which has been submitted electronically in ASCII format and is hereby incorporated by reference in its entirety. Said ASCII copy, created on Mar. 24, 2017, is named 701039-080033-US_SL.txt and is 553 bytes in size.

FIELD OF THE DISCLOSURE

This invention relates to compositions for vaccine adjuvants and uses thereof for enhancing immune response to antigens and infection.

BACKGROUND

The purpose of vaccination is to generate a strong and lasting immune response providing long-term protection against infection. However, many licensed vaccines currently induce only suboptimal immunity, requiring multiple boosts to generate a robust protective response. Adjuvantation of vaccines (i.e., addition of adjuvant) enhances both antibody and cell-mediated immune responses to antigens without the required multiple boots typical of these inoculations. An immunologic adjuvant is any substance that when incorporated into a vaccine formulation acts generally to accelerate, prolong, or enhance the quality of specific immune responses to vaccine antigens. Adjuvants can be used for various purposes: (1) to enhance the immunogenicity of highly purified or recombinant antigens; (2) to reduce the amount of antigen or the number of immunizations needed for protective immunity; (3) to improve the efficacy of vaccines in newborns, the elderly or immunocompromised persons; or (4) as antigen delivery systems for the uptake of antigens by the mucosa.

Due to impairments in cell-mediated immunity, newborns and infants are markedly susceptible to infection with intracellular pathogens including bacteria such as *Listeria* spp. and viruses such as Respiratory Syncytial Virus (RSV). Prior efforts to immunize against RSV have been hampered by formalin-inactivated vaccines that induced an inadequate T-helper 1 (Th1) cell response, resulting in enhancement of the disease in newborns and infants. Indeed, inclusion of adjuvants to induce a Th1 response is associated with beneficial protection with RSV vaccines. Impaired newborn immunity, including reduced function of dendritic cells (DCs), which are key antigen-presenting cells (APCs), puts them at risk for infection and limits their Th1 responses to many vaccines. In this context, there is an unmet need for adjuvants that activate newborn DCs to facilitate the production of Th1-polarizing cytokines, resulting in T-cell activation.

Adjuvants have been used since the early 20th Century to enhance an immune response to an antigen. The concept of adjuvants arose from observations that an abscess at the inoculation site assisted the generation of higher specific antibody titers. Adjuvant activity was first demonstrated in 1926 with aluminum, when diphtheria toxoid absorbed to alum. Despite the discovery of many more potent adjuvants, such as Freund's complete adjuvant or lipopolysaccharide, aluminum-based adjuvants remain the most prominent of the vaccine enhancers. Many of the newly discovered adjuvants have proven to be unsuitable for human use, as they result in local and systemic toxicity and do not meet the rigorous standards of pre-clinical or clinical trials. The need for adjuvants as a component of vaccines is still acute, especially as newer antigens may be weak immunogens or have limited availability. More recently, approvals have been obtained in Europe for MF59, a detergent-stabilized oil-in-water emulsion, as an adjuvant component of flu vaccine for elderly patients (Fluad®, Novartis Vaccines) and AS04 (combination of alum and monophosphoryl lipid A (MPLA), GlaxoSmithKline) as the adjuvant for a viral vaccines (hepatitis B, HPV).

Other categories of vaccine adjuvants in development, testing, or use include the following: Mineral salts-e.g., aluminum hydroxide ("alum"), aluminum phosphate, calcium phosphate; Oil emulsions-e.g., MF59; Particulate adjuvants-e.g., virosomes, ISCOMS (structured complex of saponins and lipids); Microbial derivatives-e.g., MPLA™ (monophosphoryl lipid A), CpG motifs, modified toxins; Plant derivatives-e.g., saponins (QS-21); Endogenous immunostimulatory adjuvants-e.g., cytokines.

SUMMARY

Embodiments of the present disclosure are combinatorial compositions that improve or stimulate the immune response. When used in conjunction with antigens as combination adjuvant compositions, the combination adjuvants to improve vaccine efficacy. The combinatorial compositions are also useful for preventing or treating infections. The inventors have discovered that dual synergy stimulation with Toll-like receptor agonists (TLRAs) and C-type lectin agonists (CLRAs) can overcome the reduced response of newborn DCs to common vaccine formulations and thereby enable vaccinations at a younger age. The inventors also found that dual synergy activation through certain TLRs and CLRs can induce enhanced activation of in adult DCs, but the specific combinations of TLR(s)/CLR(s) are different for the different age group. For newborns particularly, dual stimulation through the receptors Mincle and TLR8, or through the receptors Dectin-1 and TLR4 is optimal for the induction of Th1-polarizing cytokines, IFN-γ and IL-12p70 cytokines, and for the priming of naïve T cells to differentiate into IFN-γ-producing T cells. The DCs that make these Th1 cytokines actually induce a greater amount of Th1 differentiation from T cells, which is signified by the production of IFN-γ by these T cells. These cytokines and the induction of naïve T cells differentiation are important for adaptive immune responses and host defense against intracellular pathogens, and are usually minimally produced by neonatal cells. The synergistic effects of the TLRs with CLRs were associated with enhanced activation of the NF-kB and NLRP3 inflammasome pathways.

Accordingly, combinatorial activation of TLRAs and the endocytic receptors Mincle or Dectin-1 (CLRAs) is a powerful approach to induce Th1-mediated immunity in newborns, infants and also adults.

In addition, because both the TLR and CLR pathways are activated, these combinatorial compositions comprising TLR and CLR agonists are also ideal as "stand alone" immunomodulators to prevent or treat infections in newborns, infants and also adults. For example, in an immunocompromised individual.

Accordingly, it is the objective of this disclosure to provide combinatorial compositions for the purpose of inducing and/or enhancing the Th1-mediated immunity in a subject. The subject can be a newborn, an infant, a child younger than 12 years old, an elderly subject over 65 years old, or any subject in need of inducing and/or enhancing the Th1-mediated immunity. When used in conjunction with antigens, the combinatorial compositions are referred to as combinatorial adjuvant compositions or vaccine adjuvant compositions.

It is also the objective of this disclosure to provide combinatorial adjuvant compositions for the purpose of inducing and/or enhancing the Th1-mediated immunity in a subject to an antigen.

It is also the objective of this disclosure to provide combinatorial compositions for the purpose of priming and/or inducing the priming of naïve T cells to differentiate into IFN-γ-producing T cells.

It is also the objective of this disclosure to provide combinatorial compositions for the purpose of inducing and/or enhancing the Th1-mediated immunity in newborns. When used in conjunction with antigens, the combinatorial compositions are referred to as combinatorial adjuvant compositions or vaccine adjuvant compositions.

It is also the objective of this disclosure to provide combinatorial compositions for the purpose of inducing and/or enhancing the Th1-mediated immunity in newborns to an antigen.

It is also the objective of this disclosure to provide combinatorial TLR/CLR agonists compositions for the purpose of preventing infection in a subject, for example, in a subject who is immune compromise, or has weakened immune system or response, or has a defect in the immune system. For example, the very young or very old, one who is diabetic, one with a weakened immune system, one prone to infections, or one who has HIV.

It is also the objective of this disclosure to provide combinatorial TLR/CLR agonists compositions for the purpose of treating infection in a subject.

It is also the objective of this disclosure to provide combinatorial adjuvant compositions for the purpose of enhancing the immune response in a subject. The subject can be newborns, infants, the elderly or any subject in need of enhancing the immune system. For example, in a subject who is immune compromise, or has weakened immune system or response, or has a defect in the immune system.

It is also the objective of this disclosure to provide combinatorial adjuvant compositions for the purpose of enhancing the immune response in a subject to an antigen.

It is also the objective of this disclosure to provide a method of inducing and/or enhancing the Th1-mediated immunity in a subject, e.g., newborns.

It is also the objective of this disclosure to provide a method of inducing and/or enhancing the Th1-mediated immunity in a subject to an antigen.

It is also the objective of this disclosure to provide a method of enhancing the immune response in a subject.

It is also the objective of this disclosure to provide a method of enhancing the immune response in a subject to an antigen.

Accordingly, in one embodiment, provided herein is a combinatorial composition comprising at least one TLR4 agonist and at least one Dectin-1A agonist, wherein the at least TLR4 agonist is selected from monophosphoryl lipid A (MPLA) or glycopyranosyl lipid A (GLA).

In one embodiment, provided herein is a combinatorial composition comprising at least one TLR7/8 agonist and at least one Mincle agonist.

In some embodiments, when the combinatorial compositions are used in conjunction with antigens, the combinatorial compositions are referred to as combinatorial adjuvant compositions or vaccine adjuvant compositions.

In one embodiment, provided herein is a vaccine composition comprising at least one antigen and a vaccine adjuvant composition described herein.

In one embodiment, provided herein is a use of at least one TLR4 agonist and at least one Dectin-1A agonist for the manufacture of a combination adjuvant composition wherein the at least TLR4 agonist is monophosphoryl lipid A (MPLA) or glycopyranosyl lipid A (GLA).

In one embodiment, provided herein is a use of at least one TLR7/8 agonist and at least one Mincle agonist for the manufacture of a combination adjuvant composition.

In one embodiment, provided herein is a use of at least one TLR4 agonist and at least one Dectin-1A agonist for (i) enhancing an immune response in a subject; (ii) enhancing an immune response to a commercial vaccine in a subject, (iii) for inducing and/or enhancing the Th-1 mediated immunity in a subject; (iv) for preventing an infection in a subject; or (v) for treating an infection in a subject, wherein the at least TLR4 agonist is selected from MPLA or GLA.

In one embodiment, provided herein is a use of a combinatorial composition comprising at least one TLR4 agonist and at least one Dectin-1A agonist for (i) enhancing an immune response in a subject; (ii) enhancing an immune response to a commercial vaccine in a subject, (iii) for inducing and/or enhancing the Th-1 mediated immunity in a subject; (iv) for preventing an infection in a subject; or (v) for treating an infection in a subject, wherein the at least TLR4 agonist is selected from MPLA or GLA.

In one embodiment, provided herein is a use of at least one TLR7/8 agonist and at least one Mincle agonist for (i) enhancing an immune response in a subject; (ii) enhancing an immune response to a commercial vaccine in a subject, (iii) for inducing and/or enhancing the Th-1 mediated immunity in a subject; (iv) for preventing an infection in a subject; or (v) for treating an infection in a subject.

In one embodiment, provided herein is a use of at least one TLR4 agonist and at least one Dectin-1A agonist for the synergistic enhanced activation of the NF-kB and NLRP3 inflammasome pathways, and/or the priming or induction of naïve T cells to differentiate into IFN-γ-producing T cells.

In one embodiment, provided herein is a use of a combinatorial composition comprising at least one TLR7/8 agonist and at least one Mincle agonist for (i) enhancing an immune response in a subject; (ii) enhancing an immune response to a commercial vaccine in a subject, (iii) for inducing and/or enhancing the Th-1 mediated immunity in a subject; (iv) for preventing an infection in a subject; or (v) for treating an infection in a subject.

In one embodiment, provided herein is a use of at least one TLR7/8 agonist and at least one Mincle agonist for the synergistic enhanced activation of the NF-kB and NLRP3 inflammasome pathways, and/or the priming or induction of naïve T cells to differentiate into IFN-γ-producing T cells.

In one embodiment, provided herein is a method of inducing the production of Th1-polarizing cytokines, IFN-γ and/or IL-12p70 cytokines in dendritic cells (DCs), and/or priming or inducing naïve T cells to differentiate into IFN-γ-producing T cells comprising contacting dendritic cells with a combinatorial composition comprising at least one TLR4 agonist and at least one Dectin-1 agonist, wherein the at least TLR4 agonist is selected from MPLA or GLA.

In one embodiment, provided herein is a method of inducing the production of Th1-polarizing cytokines, IFN-γ and/or IL-12p70 cytokines in DCs, and/or priming or inducing naïve T cells to differentiate into IFN-γ-producing T cells comprising contacting the dendritic cells with a combinatorial composition comprising at least one TLR7/8 agonist and at least one Mincle agonist.

In one embodiment, provided herein is a method of inducing and/or enhancing the Th1-mediated immunity in a subject, the method comprising administering to the subject a vaccine adjuvant composition comprising at least one TLR4 agonist and at least one Dectin-1 agonist, wherein the at least TLR4 agonist is selected from MPLA or GLA. In some embodiments, the subject is a newborn, an infant, an elderly subject or an immune compromised subject.

In some embodiments, inducing and/or enhancing the Th1-mediated immunity in a subject comprises priming or inducing naïve T cells to differentiate into IFN-γ-producing T cells.

In one embodiment, provided herein is a method of inducing and/or enhancing the Th1-mediated immunity in a subject to an antigen, the method comprising administering to the subject a combinatorial composition comprising at least one TLR4 agonist and at least one Dectin-1 agonist with the antigen, wherein the at least TLR4 agonist is selected from MPLA or GLA. In some embodiments, the subject is a newborn, an infant, an elderly subject or an immune compromised subject.

In one embodiment, provided herein is a method of inducing and/or enhancing the Th1-mediated immunity in newborns, the method comprising administering to the newborn a combinatorial composition comprising at least one TLR4 agonist and at least one Dectin-1 agonist, wherein the at least TLR4 agonist is selected from MPLA or GLA.

In one embodiment, provided herein is a method of inducing and/or enhancing the Th1-mediated immunity in newborns to an antigen, the method comprising administering to the newborn a combinatorial composition comprising at least one TLR4 agonist and at least one Dectin-1 agonist with the antigen, wherein the at least TLR4 agonist is selected from MPLA or GLA.

In one embodiment, provided herein is a method of enhancing an immune response in a subject comprising administering to the subject a combinatorial composition comprising at least one TLR4 agonist and at least one Dectin-1 agonist, wherein the at least TLR4 agonist is selected from MPLA or GLA.

In one embodiment, provided herein is a method of enhancing immune response to an antigen in a subject comprising administering to the subject a combinatorial composition comprising at least one TLR4 agonist and at least one Dectin-1 agonist with the antigen, wherein the at least TLR4 agonist is selected from MPLA or GLA.

In one embodiment, provided herein is a method of preventing or treating an infection in a subject comprising enhancing an immune response and/or enhancing the Th1-mediated immunity in the subject. In some embodiments, the subject is a newborn, an infant, a diabetic, an elderly subject or an immune compromised subject. For example, in a subject who is immune compromise, or has weakened immune system or response, or has a defect in the immune system. In one embodiment, the enhancing the immune response and/or enhancing the Th1-mediated immunity comprises administering a combinatorial composition comprising at least one TLR4 agonist and at least one Dectin-1 agonist with the antigen, wherein the at least TLR4 agonist is selected from MPLA or GLA. In some embodiments, inducing and/or enhancing the Th1-mediated immunity in a subject comprises priming or inducing naïve T cells to differentiate into IFN-γ-producing T cells. In one embodiment, inducing and/or enhancing the Th1-mediated immunity in a subject inducing the production of Th-1 polarization cytokines such as INF-γ and IL-12p70.

In one embodiment, provided herein is a method of inducing and/or enhancing the Th1-mediated immunity in a newborn or an infant, the method comprising administering to the newborn or infant a combinatorial composition comprising at least one TLR7/8 agonist and at least one Mincle agonist.

In one embodiment, provided herein is a method of inducing and/or enhancing the Th1-mediated immunity in a newborn or an infant to an antigen, the method comprising administering a combinatorial composition comprising at least one TLR7/8 agonist and at least one Mincle agonist with the antigen to the newborn or infant.

In one embodiment, provided herein is a method of inducing and/or enhancing the Th1-mediated immunity in a subject, the method comprising administering to the subject a combinatorial composition comprising at least one TLR7/8 agonist and at least one Mincle agonist. The subject can be newborns, infants, an elderly subject over 65 years old or any subject in need of enhancing the immune system, e.g., an immune compromised subject.

In one embodiment, provided herein is a method of inducing and/or enhancing the Th1-mediated immunity in a subject to an antigen, the method comprising administering a combinatorial composition comprising at least one TLR7/8 agonist and at least one Mincle agonist with the antigen to the subject.

In one embodiment, provided herein is a method of enhancing immune response in a subject comprising administering a combinatorial composition comprising at least one TLR7/8 agonist and at least one Mincle agonist to the subject. In one embodiment, the subject is a newborn or an infant.

In one embodiment, provided herein is a method of enhancing immune response to an antigen in a subject comprising administering a combinatorial composition comprising at least one TLR7/8 agonist and at least one Mincle agonist with the antigen to the subject. In one embodiment, the subject is a newborn or an infant.

In one embodiment, provided herein is a method of preventing or treating an infection in a subject comprising enhancing the immune response and/or enhancing the Th1-mediated immunity in the subject. In some embodiments, the subject is a newborn, an infant, an elderly subject or an immune compromised subject. In one embodiment, the enhancing the immune response and/or enhancing the Th1-mediated immunity comprises administering a combinatorial composition comprising at least one TLR7/8 agonist and at least one Mincle agonist to the subject.

In one embodiment, provided herein is a method of preventing an infection in a subject comprising administering a combinatorial composition comprising at least one TLR7/8 agonist and at least one Mincle agonist to the subject. In one embodiment, the subject is a newborn or an infant. In another embodiment, the subject is an elderly subject over 65 years old or an immune compromised subject.

In one embodiment, provided herein is a method of treating an infection in a subject comprising administering a combinatorial composition comprising at least one TLR7/8 agonist and at least one Mincle agonist to the subject. In one embodiment, the subject is a newborn or an infant. In another embodiment, the subject is an elderly subject over 65 years old or an immune compromised subject.

In one embodiment, provided herein is a method of preventing an infection in a subject comprising administering a combinatorial composition comprising at least one TLR4 agonist and at least one Dectin-1 agonist to the subject, wherein the at least TLR4 agonist is selected from MPLA or GLA. In one embodiment, the subject is a newborn or an infant. In another embodiment, the subject is an elderly subject over 65 years old or an immune compromised subject.

In one embodiment, provided herein is a method of treating an infection in a subject comprising administering a combinatorial composition comprising at least one TLR4 agonist and at least one Dectin-1 agonist to the subject, wherein the at least TLR4 agonist is selected from MPLA or GLA. In one embodiment, the subject is a newborn or an infant. In another embodiment, the subject is an elderly subject over 65 years old or an immune compromised subject.

In one embodiment of the vaccine adjuvant composition, vaccine or method described, the Dectin-1 agonist is a Dectin 1A agonist or a Dectin 1B agonist.

In one embodiment of the combinatorial composition or vaccine adjuvant composition, vaccine or method described, the at least one TLR7/8 agonist is any agent that would activate the receptor TLR7 and/or TLR8. In some embodiments, the at least one TLR7/8 agonist includes but is not limited to gardiquimod, imiquimod, imidazoquinoline compound R848 (resiquimod), a benzazepine TLR8 agonist VTX-294, 3M-052, 3M compounds listed U.S. Pat. No. 7,799,800, compounds CL087, CL097, and CL075 of INVITROGEN™. VTX-294 is a benzazepine, provided by VentiRx Pharmaceuticals. 3M-052 is an imidazoquinoline compound from 3M, N-(4-{[4-amino-2-butyl-1H-imidazo [4,5-c]quinolin-1-yl]oxy}butyl)octadecanamide. See "Vaccine adjuvant activity of 3M-052: An imidazoquinoline designed for local activity without systemic cytokine induction," by Dmitri Smirnov et al., in Vaccine, Volume 29, Issue 33, 26 Jul. 2011, Pages 5434-5442; and in "Intratumoral immunotherapy with the TLR7/8" by Dmitri Smirnov et al., in Journal for ImmunoTherapy of Cancer 2013, 1(Suppl 1):P138.

In one embodiment of any one of the combinatorial composition or vaccine adjuvant composition, vaccine or method described, the at least one TLR7/8 agonist is selected from the group consisting of gardiquimod, imiquimod, imidazoquinoline compound R848 (resiquimod), CL087, CL097, and CL075.

In one embodiment of any one of the combinatorial composition or vaccine adjuvant composition, vaccine or method described, the at least one Mincle agonist includes but is not limited to heat-killed *Mycobacterium tuberculosisis* (HKMT), trehalose-6,6-dibehenate (TDB), Trehalose-6,6-dibehenate formulated with Kolliphor® HS 15 (TDB-HS15), and trehalose-6,6'-dimycolate (TDM).

In one embodiment of any one of the combinatorial composition or vaccine adjuvant composition, vaccine or method described, the at least one Mincle agonist is selected from a group consisting of HKMT, TDB, TDB-HS15, and TDM.

In one embodiment of any one of the combinatorial composition or vaccine adjuvant composition, vaccine or method described, the vaccine adjuvant composition further comprises a pharmaceutically acceptable carrier.

In one embodiment of any one of the vaccine composition described, the at least one antigen includes but is not limited to an antigen that is a live attenuated micro-organism that causes known diseases, an antigen that is an inactivated or killed micro-organism that causes known diseases, an antigen that is an inactivated toxin that is produced by a micro-organism that causes known diseases, or an antigen that is a subunit or a conjugate of a subunit of a micro-organism that causes known diseases.

In one embodiment of any one of the vaccine composition described, the combination adjuvant can be paired with a broad range of antigens, including but not limited to all the antigens that are known in the art for vaccination against known diseases, that is, all antigens that the combination adjuvant can pair with. For example, respiratory syncytial virus (RSV) F protein, RSV pre-fusion (F) protein, RSV Nucleoprotein N, HIV-GAG, HIV-gp140, or various outer membrane proteins from Gram-positive, Gram-negative or myco-bacteria.

In one embodiment of any one of the vaccine composition described, the at least one antigen includes but is not limited to an antigen against measles, mumps, rubella, chicken pox (Varicella), shingles (Zoster), Influenza (e.g. *Haemophilus influenza* type b), pneumonia (Pneumococcal diseases caused by *Streptococcus pneumoniae*), pneumococcal bacteremia, meningitis (Meningococcal diseases caused by the bacterium, *Neisseria meningitidis*), Rotavirus, diphtheria, tetanus, pertussis (whooping cough), polio (IPV), smallpox, HIV/AIDS, malaria, and Leishmaniasis, Hepatitis A, Hepatitis B, Hepatitis C, Anthrax, Yellow fever, rabies, Human papillomavirus (HPV), *Clostridium tetani* bacterium neurotoxin (tetanospasmin), tuberculosis, Dengue, typhoid, and Japanese encephalitis.

In one embodiment of any one of the vaccine composition described, the at least one antigen is selected from a group consisting of an antigen against measles, mumps, rubella, chicken pox (Varicella), shingles (Zoster), Influenza (e.g. *Haemophilus influenza* type b), pneumonia (Pneumococcal diseases caused by *Streptococcus pneumoniae*), pneumococcal bacteremia, meningitis (Meningococcal diseases caused by the bacterium, *Neisseria meningitidis*), Rotavirus, diphtheria, tetanus, pertussis (whooping cough), polio (IPV), smallpox, HIV/AIDS, malaria, and Leishmaniasis, Hepatitis A, Hepatitis B, Hepatitis C, Anthrax, Cholera, Yellow fever, rabies, Human papillomavirus (HPV), *Clostridium tetani* bacterium neurotoxin (tetanospasmin), typhoid, and Japanese encephalitis.

In one embodiment of any one of the vaccine composition described, the combinatorial composition or vaccine adjuvant composition is in an amount of about 85 to 99% of the mass of the vaccine.

In one embodiment of any one of the vaccine composition described, the at least TLR4 agonist is in the range of about 0.1 to about 5% of the mass of the fraction.

In one embodiment of any one of the vaccine composition described, the at least TLR4 agonist is in the range of about 0.1 to about 3% of the mass of the fraction.

In one embodiment of any one of the vaccine composition described, the at least Dectin-1 agonist is in the range of about 0.1 to about 5% of the mass of the fraction.

In one embodiment of any one of the vaccine composition described, the at least Dectin-1 agonist is in the range of about 0.1 to about 3% of the mass of the fraction.

In one embodiment of any one of the vaccine composition described, the vaccine composition further comprises alum-hydroxide as a co-adjuvant.

In one embodiment of any one of the vaccine composition described, the concentration of the adjuvant composition is about 150 µg-about 150 mg/single dose, wherein about 150 µg-about 150 mg is the dosage for the combined agonists in the composition.

In some embodiments of any one of the compositions described, the dose of TDB is about 10-100 microgram/ml, the dose of R848 is about 1-50 micromolar, the dose of Zymosan/Dectin is about 10-100 microgram/ml, and the dose of MPLA or GLA is about 10 nanogram/ml-1 microgram/ml.

In one embodiment of any one of the vaccine compositions or combination adjuvant composition described, the vaccine composition or combination adjuvant composition is formulated in an oil-in-water emulsion. In one embodiment of any one of the vaccine compositions or combination adjuvant composition described, the vaccine composition or combination adjuvant composition is formulated as a nanoparticle, such as a polymersome, In one embodiment of any one of the methods described, the subject is a human adult. In another embodiment of any one of the method described, the subject is a human newborn. In another embodiment of any one of the method described, the subject is a non-human mammal. The subject can be newborns, infants, the elderly or any subject in need of enhancing the immune system. For example, in a subject who is immune compromise, or has weakened immune system or response, or has a defect in the immune system.

In one embodiment of any one of the methods described, there is an induction of Th1-polarizing cytokines in the subject upon administration of the combination composition described.

In one embodiment of any one of the methods described, the Th1-polarizing cytokines are TNF-α, IFN-γ and the T-helper 17 (Th17)-polarizing cytokine IL-1β.

In one embodiment of any one of the methods described, there is an induction of IFN-γ cytokine in the subject upon administration of the combination composition described.

In one embodiment of any one of the methods described, there is an induction of TNF-α cytokine in the subject upon administration of the combination composition described.

In one embodiment of any one of the methods described, there is an induction of IL-1β cytokine in the subject upon administration of the combination composition described.

In one embodiment of any one of the methods described, there is an induction of IL-12p70 cytokine in the subject upon administration of the combination composition described.

In one embodiment of any one of the methods described, there is an induction of differentiation of naïve T cells to differentiate into IFN-γ-producing T cells in the subject upon administration of the combination composition described.

In one embodiment of any one of the methods described, there is a synergistic effect associated with an enhanced activation of the NF-kB and NLRP3 inflammasome pathways in the subject upon administration of the combination composition described.

In one embodiment of any one of the methods of inducing the production of Th1-polarizing cytokines, IFN-γ and/or IL-12p70 cytokines in dendritic cells, the Th1-polarizing cytokines are TNF-α, IFN-γ and the T-helper 17 (Th17)-polarizing cytokine IL-1β.

In one embodiment of any one of the methods of inducing the production of Th1-polarizing cytokines, IFN-γ and/or IL-12p70 cytokines in dendritic cells, the dendritic cells are immature dendritic cells.

In one embodiment of any one of the methods of inducing the production of Th1-polarizing cytokines, IFN-γ and/or IL-12p70 cytokines in dendritic cells, the dendritic cells are adult DCs, newborn DCs, or infant DCs.

In one embodiment of any one of the methods of inducing the production of Th1-polarizing cytokines, IFN-γ and/or IL-12p70 cytokines in dendritic cells, the contacting is in vivo, ex vivo or in vitro.

In one embodiment of any one of the methods of inducing the production of Th1-polarizing cytokines, IFN-γ and/or IL-12p70 cytokines in dendritic cells, the contacting is in vivo in the subject.

In one embodiment of any one of the methods, the method further comprises selecting a subject for treatment of infection, for prevention of infection, for enhancing the immune system or response in the subject, for inducing Th-1 meditate immunity and/or vaccination. For example, the subject selected for any one of the procedures is a newborn, an infant, a child, an adolescent, an elderly subject or an immune compromised or immune deficient subject. It is envisioned that the combinatorial compositions described herein would enhance the immune system in the subject.

BRIEF DESCRIPTION OF THE DRAWINGS

FIG. 2A shows adult MoDCs were incubated with different combinations of TLRAs and CLRAs. The black lines indicate the amount of secreted TNF-α after stimulation with the TLRA alone, as indicated on the x-axis. The other shades of gray lines indicate TNF-α secretion after stimulation with the TLRA (x-axis) in combination with a CLRA (other shades of gray indicated in the legend).

FIG. 2B shows newborn MoDCs were incubated with different combinations of TLRAs and CLRAs. The black lines indicate the amount of secreted TNF-α after stimulation with the TLRA alone, as indicated on the x-axis. The other shades of gray lines indicate TNF-α secretion after stimulation with the TLRA (x-axis) in combination with a CLRA (other shades of gray indicated in the legend).

FIG. 2C shows the combination of MPLA with zymosan induces synergistic activation. Dual stimulation of MoDCs with a combination of MPLA and Zymosan induces TNF-α to adult-like levels in newborns (MPLA low, 10 ng/ml; MPLA high, 1 µg/ml; Zymosan, 100 µg/ml).

FIG. 2D shows the combination of R848 with TDB induces synergistic activation. Newborn and adult MoDCs incubated with a combination of R848 and TDB (R848 low, 1 µM; R848 high, 50 µM; TDB, 10 µg/ml) show increased production of TNF-α.

FIG. 2E shows the secretion of TNF-α in response to single TLRAs and CLRAs. Newborns are impaired in the production of TNF-α. (Students' t-test; $*p<0.05$, $p<0.01$ and $*p<0.001$)

FIG. 2F shows the Bar diagram representation of TNF-α secretion in response to MPLA, Zymosan or combination and R848, TDB or combination. Combinations of CLRA+TLRA that induce significantly more TNF-α than the TLRA alone are indicated with stars (Students' t-test; $*p<0.05$, $p<0.01$ and $*p<0.001$)

FIG. 4A shows that newborn (i) and adult (ii) MoDCs stimulated with MPLA (in red lines) (1 µg/ml) and/or Zymosan (in blue lines) (100 µg/ml).

FIG. 4B shows that newborn (i) and adult (ii) MoDCs stimulated with R848 (in red lines) (50 µM) and/or TDB (in blue lines) (10 µg/ml).

FIGS. 6A-6-H show that synergistic stimulation of newborn MoDCs promotes the polarization of naïve CD4+ T cells to Th1 cells. Naïve (CD4+CD45RA+CD45RO−) T cells were isolated and activated for 6 days with CD3/CD28 beads, in the presence of culture supernatants of autologous MoDCs activated with agonists as indicated. After 6 days, the production of cytokines was analyzed by 6 h incubation following the addition of Brefeldin A. Cells were subsequently fixed, permeabilized and stained for IFN-γ, IL-4, IL-10 and IL-17 using fluorescent antibodies. (FIGS. 6A and 6E) Relative percentage of IFN-γ producing cells. (FIGS. 6B and 6F) Relative percentage of IL-4 producing cells. (FIGS. 6C and 6G) Percentages of IFN-γ producing cells (FIGS. 6A and 6E) were divided by the percentage of IL-4 producing cells (FIGS. 6B and 6F) to obtain the ration of Th1/Th2 cells. (FIGS. 6D and 6H) Relative percentages of IFN-γ, IL-4-, IL-10- and IL-17-producing cells. Statistical comparisons employed the Students' t-test. $*p<0.05$, $p<0.01$ and $*p<0.001$.

DETAILED DESCRIPTION

Definitions of Terms

Figure 1:
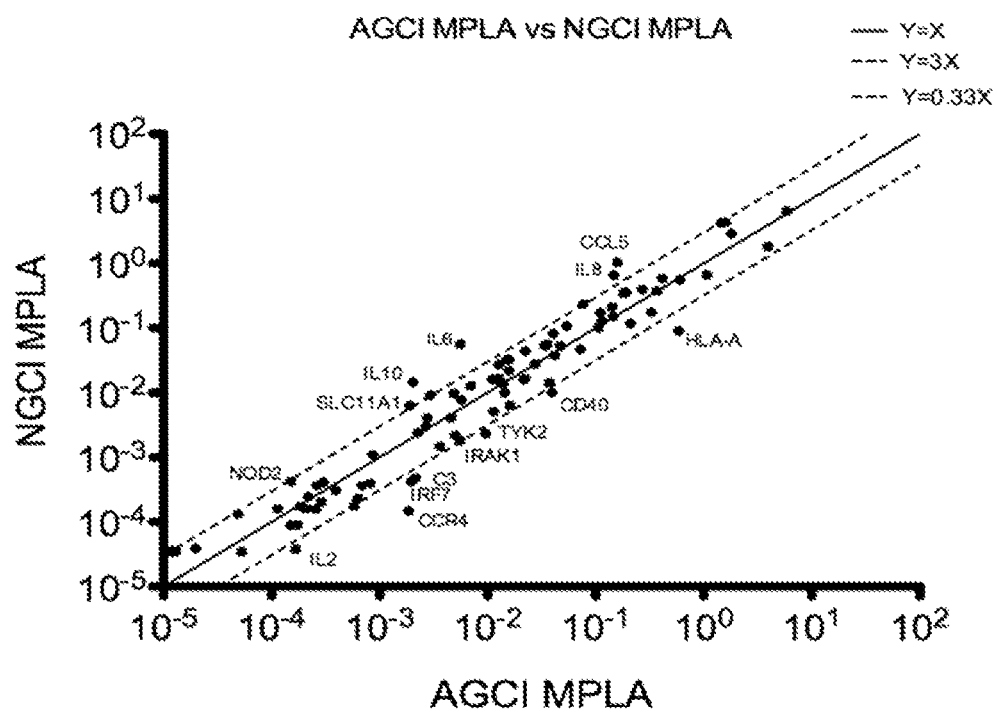
FIG. 1 shows that neonatal MoDCs demonstrate a distinct MPLA-induced innate immune transcriptome. Messenger RNA ΔcT levels of newborn and adult MoDCs are shown. MoDCs were stimulated with MPLA (1 µg/ml) for 24 hours. Total RNA was isolated from lysates of cells and cDNA was synthesized from RNA and analyzed by quantitative RT-PCR. Delta-cT levels of adult cells are plotted against their newborn counterparts (dashed lines indicate 3-fold change). Newborn MoDCs expressed greater levels of mRNA encoding IL-6 (Th2/Th17) and IL-10 (anti-inflammatory) but less of mRNAs encoding CCR4, IRAK1 and IRF7, amongst others. IRAK1 is an important signaling component downstream of TLR activation. N=2 per group.

As used herein in the context of immunization, immune response and vaccination, the term "adjuvant" refers to any substance than when used in combination with a specific antigen that produces a more robust immune response than the antigen alone.

In certain embodiments, the "adjuvant" is any substance that when incorporated into a vaccine formulation acts generally to accelerate, prolong, or enhance the quality of specific immune responses to the vaccine antigen(s).

As used herein in the context of immunization, immune response and vaccination, the term "combination adjuvants" refers to a composition that is made up of more than one distinct adjuvant.

The term "vaccine composition" used herein is defined as composition used to elicit an immune response against an antigen within the composition in order to protect or treat an organism against disease. In some embodiment, the vaccine composition is a suspension of attenuated or killed microorganisms (e.g., viruses, bacteria, or rickettsiae), or of antigenic proteins derived from them, administered for prevention, amelioration, or treatment of infectious diseases. The terms "vaccine composition" and "vaccine" are used interchangeably.

As used herein, the term "antigen" refers to any substance capable of inducing a specific immune response and of reacting with the products of that response, i.e., with specific antibody or specifically sensitized T lymphocytes, or both. Antigens may be soluble substances, such as toxins and foreign proteins, or particulates, such as bacteria and tissue cells.

As used herein, the term "newborn" refers to an infant from the time of birth through the 28th day of life. In one embodiment, the newborn is a human infant. In the embodiment that the newborn is a premature, the $28^{th}$ day is extended to include the number of days of premature birth.

As used herein, the term "the time of birth" in reference to a newborn refers to birth of the newborn anywhere after 35 weeks in gestation.

As used herein, the term "infant" refers to a young from the time of birth to one year of age.

As used herein, the term "comprising" means that other elements can also be present in addition to the defined elements presented. The use of "comprising" indicates inclusion rather than limitation.

The term "consisting of" refers to combinatorial compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment of the invention.

The term "cell mediated immunity" or "CMI" as used herein refers to an immune response that does not involve antibodies or complement but rather involves the activation of, for example, macrophages, natural killer cells (NK), antigen-specific cytotoxic T-lymphocytes (T-cells), and the release of various cytokines in response to a target antigen. Stated another way, CMI refers to immune cells (such as T cells and lymphocytes) which bind to the surface of other cells that display a target antigen (such as antigen presenting cells (APS)) and trigger a response. The response may involve either other lymphocytes and/or any of the other white blood cells (leukocytes) and the release of cytokines. Cellular immunity protects the body by: (i) activating antigen-specific cytotoxic T-lymphocytes (CTLs) that are able to destroy body cells displaying epitopes of foreign antigen on their surface, such as virus-infected cells and cells with intracellular bacteria; (2) activating macrophages and NK cells, enabling them to destroy intracellular pathogens; and (3) stimulating cells to secrete a variety of cytokines that influence the function of other cells involved in adaptive immune responses and innate immune responses.

The term "immune cell" as used herein refers to any cell which can release a cytokine in response to a direct or indirect antigenic stimulation. Included in the term "immune cells" herein are lympocytes, including natural killer (NK) cells, T-cells (CD4+ and/or CD8+ cells), B-cells, macrophages and monocytes, Th cells; Th1 cells; Th2 cells; Tc cells; leukocytes; dendritic cells; macrophages; mast cells and monocytes and any other cell which is capable of producing a cytokine molecule in response to direct or indirect antigen stimulation. Typically, an immune cell is a lymphocyte, for example a T-cell lymphocyte.

The term "cytokine" as used herein refers to a molecule released from an immune cell in response to stimulation with an antigen. Examples of such cytokines include, but are not limited to: GM-CSF; IL-1; IL-1; IL-2; IL-3; IL-4; IL-5; IL-6; IL-7; IL-8; IL-10; IL-12; IFN-; IFN-; IFN-; MIP-1; MIP-1; TGF-; TNF and TNF. The term "cytokine" does not include antibodies.

The term "in vivo" refers to assays or processes that occur in an animal.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras, food animals such as cows, pigs, and sheep; ungulates such as deer and giraffes; rodents such as mice, rats, hamsters and guinea pigs; and bears. In some embodiments, a mammal is a human.

The term "pharmaceutically acceptable" refers to compounds and compositions which may be administered to mammals without undue toxicity. The term "pharmaceutically acceptable carriers" excludes tissue culture medium. Exemplary pharmaceutically acceptable salts include but are not limited to mineral acid salts such as hydrochlorides, hydrobromides, phosphates, sulfates, and the like, and the salts of organic acids such as acetates, propionates, malonates, benzoates, and the like.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

As used herein, the terms "administering" or "administration" refers to the placement of the vaccine adjuvant composition or combinatorial composition described herein into a subject by a method or route which results in an immune response, for example, in inducing cytokine production. In one embodiment, administering the combination adjuvants induces Th1-polarizing cytokines, IFN-γ and IL-12p70 cytokines productions in dendritic cells. The vaccine adjuvant or composition can be administered by any appropriate route which results in an effectuate vaccination in the subject. Most often, it is by injection or oral ingestion.

Unless otherwise explained, all technical and scientific terms used herein have the same meaning as commonly understood by one of ordinary skill in the art to which this disclosure belongs. Definitions of common terms in immunology and molecular biology may be found in The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties. Further, unless otherwise required by context, singular terms shall include pluralities and plural terms shall include the singular.

Unless otherwise stated, the present invention was performed using standard procedures known to one skilled in the art, for example, in Michael R. Green and Joseph Sambrook, Molecular Cloning: A Laboratory Manual (4th ed.), Cold Spring Harbor Laboratory Press, Cold Spring Harbor, N.Y., USA (2012); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Meolcular Biology, Vo. 203, 2003, Transgenic Mouse, edited by Marten H. Hofker and Jan van Deursen, which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Embodiments of the present disclosure are combinatorial compositions for improving vaccine efficacy, for enhancing an immune response, and for preventing or treating an infection. When the combinatorial compositions are used in conjunction with antigens, for example, during vaccination, the combinatorial compositions are referred to as combinatorial adjuvant compositions or vaccine adjuvant compositions.

The combinatorial compositions induce Th1-polarizing cytokines in both adult DCs and newborn DCs. The inventors have discovered that dual synergistic stimulation with Toll-like receptor agonists (TLRAs) and C-type lectin agonists (CLRAs) can overcome the reduced response of newborn DCs to common vaccine formulations and thereby enable vaccinations at a younger age. The inventors also found that dual activation through certain TLRs and CLRs can induce enhanced activation of not only adult DCs, but can also enhance newborn DC activation. Particularly, dual stimulation through the receptors Mincle and TLR8, or through the receptors Dectin-1 and TLR4 is optimal for the induction of Th1-polarizing cytokines, IFN-γ and IL-12p70 cytokines DCs. Furthermore, the dual synergistic stimulation also primes and induce naïve T cells to differentiate into IFN-γ-producing T cells. The synergistic effects of the TLRs with CLRs were associated with enhanced activation of the NF-kB and NLRP3 inflammasome pathways, and are important for adaptive immune responses and host defense against intracellular pathogens, and are usually minimally produced by neonatal cells.

Accordingly, in one embodiment, provided herein is a combinatorial composition or vaccine adjuvant composition comprising at least one TLR4 agonist and at least one Dectin-1 agonist, wherein the at least TLR4 agonist is selected from monophosphoryl lipid A (MPLA) or glycopyranosyl lipid A (GLA). In one embodiment, the composition further comprises at least one TLR7/8 agonist and/or at least one Mincle agonist.

In one embodiment, provided herein is a combinatorial composition or a vaccine adjuvant composition comprising at least one TLR7/8 agonist and at least one Mincle agonist. In one embodiment, the composition further comprises at least at least one TLR4 agonist and/or at least one Dectin-1 agonist, wherein the at least TLR4 agonist is selected from MPLA or GLA.

In one embodiment, provided herein is a vaccine composition comprising at least one antigen and a vaccine adjuvant composition described herein.

In one embodiment, the vaccine composition comprising at least one antigen, at least one TLR4 agonist and at least one Dectin-1 agonist, wherein the at least TLR4 agonist is selected from MPLA or GLA. In one embodiment, the vaccine adjuvant composition further comprises at least one TLR7/8 agonist and/or at least one Mincle agonist.

In one embodiment, the vaccine composition comprising at least one antigen, at least one TLR7/8 agonist and at least one Mincle agonist. In one embodiment, the vaccine adjuvant composition further comprises at least at least one TLR4 agonist and/or at least one Dectin-1 agonist, wherein the at least TLR4 agonist is selected from MPLA or GLA.

In one embodiment, provided herein is a method of inducing the production of Th1-polarizing cytokines in dendritic cells (DCs) comprising contacting a DC with a combinatorial composition, wherein the Th1-polarizing cytokines are IFN-γ and/or IL-12p70 cytokines, and wherein the combinatorial composition comprising at least one antigen, at least one TLR4 agonist and at least one Dectin-1 agonist, wherein the at least TLR4 agonist is selected from MPLA or GLA. In one embodiment, the composition further comprises at least one TLR7/8 agonist and/or at least one Mincle agonist.

In one embodiment, provided herein is a method of priming and inducing the differentiation of naïve T cells into IFN-γ-producing T cells comprising contacting a population of naïve T cells with a combinatorial composition, wherein the combinatorial composition comprising at least one antigen, at least one TLR4 agonist and at least one Dectin-1 agonist, wherein the at least TLR4 agonist is selected from MPLA or GLA. In one embodiment, the composition further comprises at least one TLR7/8 agonist and/or at least one Mincle agonist.

In one embodiment, provided herein is a method of inducing the production of Th1-polarizing cytokines in DCs comprising contacting a dendritic cell with a combinatorial composition, wherein the Th1-polarizing cytokines are IFN-γ and/or IL-12p70 cytokines, and wherein the combinatorial composition comprising at least one antigen, at least one TLR7/8 agonist and at least one Mincle agonist. In one embodiment, the composition further comprises at least one TLR4 agonist and/or at least one Dectin-1 agonist, wherein the at least TLR4 agonist is selected from MPLA or GLA.

In one embodiment, provided herein is a method of priming and inducing the differentiation of naïve T cells into IFN-γ-producing T cells comprising contacting a population of naïve T cells with a combinatorial composition, wherein the combinatorial composition comprising at least one antigen, at least one TLR7/8 agonist and at least one Mincle agonist. one embodiment, the composition further comprises at least one TLR4 agonist and/or at least one Dectin-1 agonist, wherein the at least TLR4 agonist is selected from MPLA or GLA.

In one embodiment, provided herein is a method of inducing the production of Th1-polarizing cytokines in DCs comprising contacting a DC with a combinatorial composition described herein. In one embodiment, the Th1-polarizing cytokines are IFN-γ and/or IL-12p70 cytokines.

In one embodiment, provided herein is a method of priming and inducing the differentiation of naïve T cells into IFN-γ-producing T cells comprising contacting a population of naïve T cells with at least one of the combinatorial composition described herein.

In one embodiment, provided herein is a method of enhancing immune response to an antigen in a subject comprising administering a vaccine adjuvant composition comprising at least one TLR4 agonist and at least one Dectin-1 agonist with the antigen to the subject, wherein the at least TLR4 agonist is selected from MPLA or GLA. In one embodiment, the composition further comprises at least one TLR7/8 agonist and/or at least one Mincle agonist.

In one embodiment, provided herein is a method of enhancing immune response to an antigen in a subject comprising administering a vaccine adjuvant composition comprising at least one TLR7/8 agonist and at least one Mincle agonist with the antigen to the subject. In one embodiment, the composition further comprises at least one TLR4 agonist and/or at least one Dectin-1 agonist, wherein the at least TLR4 agonist is selected from MPLA or GLA.

In one embodiment, provided herein is a method of inducing and/or enhancing the Th1-mediated immunity in newborns or infants to an antigen, the method comprising administering a vaccine adjuvant composition comprising at least one TLR4 agonist and at least one Dectin-1 agonist with the antigen to the newborn or infant, wherein the at least TLR4 agonist is selected from MPLA or GLA. In one embodiment, the composition further comprises at least one TLR7/8 agonist and/or at least one Mincle agonist.

In one embodiment, provided herein is a method of inducing and/or enhancing the Th1-mediated immunity in newborns or infants to an antigen, the method comprising administering a vaccine adjuvant composition comprising at least one TLR7/8 agonist and at least one Mincle agonist with the antigen to the newborn or infant. In one embodiment, the composition further comprises at least one TLR4 agonist and/or at least one Dectin-1 agonist, wherein the at least TLR4 agonist is selected from MPLA or GLA.

In one embodiment, provided herein is a method of vaccinating a newborn or infant comprising administering a vaccine adjuvant composition comprising at least one TLR4 agonist and at least one Dectin-1 agonist with the antigen to the newborn or infant, wherein the at least TLR4 agonist is selected from MPLA or GLA. In one embodiment, the composition further comprises at least one TLR7/8 agonist and/or at least one Mincle agonist.

In one embodiment, provided herein is a method of vaccinating a newborn or infant comprising administering a vaccine adjuvant composition comprising at least one TLR7/8 agonist and at least one Mincle agonist in conjunction with an antigen to the newborn. In one embodiment, the composition further comprises at least one TLR4 agonist and/or at least one Dectin-1 agonist, wherein the at least TLR4 agonist is selected from MPLA or GLA.

In one embodiment, provided herein is a use of at least one TLR4 agonist and at least one Dectin-1 agonist for the manufacture of a combination adjuvant composition, wherein the at least TLR4 agonist is selected from monophosphoryl lipid A (MPLA) or glycopyranosyl lipid A (GLA).

In one embodiment, provided herein is a use of at least one TLR7/8 agonist and at least one Mincle agonist for the manufacture of a combination adjuvant composition.

In one embodiment, provided herein is a use of at least one TLR4 agonist and at least one Dectin-1A agonist for enhancing an immune response to a commercial vaccine in a subject, wherein the at least TLR4 agonist is selected from MPLA or GLA.

In one embodiment, provided herein is a use of at least one TLR7/8 agonist and at least one Mincle agonist for enhancing an immune response to a commercial vaccine in a subject.

The inventors have discovered that specific combinations of Toll-like receptor (TLR) agonists (TLRAs) and C-type lectin receptor (CLR) agonists (CLRAs) can induce robust activation of neonatal dendritic cells (DCs). Adjuvant formulations derived from such combinations that can activate neonatal DCs can be applied in a vaccine which is administered at birth and/or during the first 3 years after birth, or even later.

In comparison to adults, neonatal dendritic cells (DCs) demonstrate impaired responses to most vaccine adjuvants, with respect to production of T-cell activating and Th1-polarizing cytokines. Due to impairments in cell-mediated immunity, newborns and infants are markedly susceptible to infection with intracellular pathogens including bacteria such as *Listeria* spp. and viruses such as Respiratory Syncytial Virus (RSV). Prior efforts to immunize against RSV have been hampered by enhanced disease occurring from vaccination with formalin-inactivated vaccines that induced an inadequate T-helper 1 (Th1) cell response. Indeed, inclusion of adjuvants to induce a Th1 response is associated with beneficial protection with RSV vaccines. Impaired newborn immunity, including reduced function of dendritic cells (DCs), which are key antigen-presenting cells (APCs), puts them at risk for infection and limits their Th1 responses to many vaccines. In this context, there is an unmet need for adjuvants that activate newborn DCs to produce Th1-polarizing cytokines, resulting in T-cell activation. In this context, there is an unmet need for adjuvants that provide safe but robust stimulation of newborn DCs. Finding adjuvants that can provide adequate stimulation of newborn dendritic cells may lead to the development of novel "stand alone" immune-enhancing drugs and/or adjuvanted neonatal vaccines, which can reduce infection in infants and result in a significant public health benefit.

Vaccine adjuvantation can employ agonists of pattern recognition receptors (PRRs). However, Th1-polarizing responses of newborn MoDCs to some PRR agonists such as Toll-like receptor agonists (TLRAs) is impaired.(1, 2) Some C-type lectin receptor agonists (CLRAs) can activate NF-Kb through a different pathway than TLRs and can act in synergy with to TLRAs towards human adult leukocytes. (3-6).

For example, Dectin-1, a lectin family receptor for β-glucans, was shown to collaborate with TLR2 in recognizing microbes, enhances TLR-mediated activation of NFkB by β-glucan-containing particles. (9) In adult macrophages and dendritic cells, dectin-1 and TLRs are synergistic in mediating production of cytokines such as IL-12 and TNF-α. (9). Similarly, stimulation of human adult peripheral blood mononuclear cells with suboptimal doses of TLR1/2 (Pam3CSK agonist), TLR4 (LPS agonist) and TLR5 (flagellin agonist) ligands induced low levels of TNF that were greatly enhanced by activation of the Syk pathway with β-glucan. (10) Similarly, coligation of TLR7 (CL-097 agonist) or TLR9 (ODN1826 agonist) with Dectin-1 induced collaborative TNF responses in thioglycollate-elicited adult macrophages. (10).

The synergistic interactions between the Mincle and TLR2 signaling pathways in neutrophils to effectuate inflammation has been reported. (11). The co-stimulation with TLR 1/2 (via Pam3CSK4), or TLR4 (via LPS) and TLR7 (via Imiquimod) induced robust inflammatory responses in adult macrophages. (12)

The inventors therefore explored the combined activation with TLRAs and CLRAs can effectively activate neonatal MoDCs. Accordingly, the inventors screened diverse combinations of TLRAs and CLRAs for the ability to induce the Th1-polarizing cytokine TNFα. The data demonstrate novel synergy between TLR4As, including monophosphoryl lipid A (MPLA) and glycopyranosyl lipid A (GLA), and the Dectin-1A Zymosan as well as between a TLR7/8A (R848) and a MincleA (Trehalose-6,6-dibehenate, TDB) that activate neonatal MoDC secretion of T-cell activating and Th1 polarizing cytokines at adult-like levels.

Using high-throughput screening of TLR agonists and CLR agonists, the inventors have established two combinations that provide an elevated secretion of the pro-inflammatory cytokine TNF-α by newborn DCs, as compared to the sum of their individual stimulation. Their data confirm results described in the present literature that certain combinations of TLR-As and CLR-As are able to induce enhanced leukocyte activation in an adult setting.

In this disclosure the inventors report the discovery that dual stimulation through TLR4, for example, LPS or monophosphoryl lipid A (MPLA), and with the CLR Dectin-1, for example, Zymosan or beta-glucan, markedly enhances the production of the phagocyte-stimulating and Th1-polarizing cytokine TNF-α by neonatal DCs. In addition, dual stimulation through TLR7/8, for example, the imidazoquinoline R848, and with the CLR Mincle, for example, Trehalose-6,6-dibehenate, also markedly enhance TNF-α production by neonatal DCs. This has been confirmed in N=3 newborns and N=3 adults with experiments designed to more broadly characterize the scope of cytokine induction.

In the past, the industry used aluminum salts as an adjuvant, but as newer vaccines are developed, industry is also looking for alternatives.

There are advantages to using adjuvants together with vaccines. For example, adjuvant additions to a vaccines enhance both antibody and cell-mediated immune responses to antigens without the required multiple boots typical of these inoculations. Use of adjuvants can reduce the amount or dosage of antigens at each vaccination required to elicit the desired immune responses.

It is also envisioned that the methods described herein can be used as prophylaxis new vaccine adjuvant has been found to be far more effective compared to traditional adjuvant new vaccines such as the pentavalent vaccine targeting meningitis, or those against dengue and pneumococcal diseases, vaccines against meningitis, polio, diphtheria, tetanus and hepatitis but also holds promise against HIV, tuberculosis and malaria.

Newer vaccines include synthetic, recombinant or highly purified subunit antigens that are weakly immunogenic. Therefore vaccine formulations often require adjuvants for better immunological efficiency. Immuno-modulators obtained from different sources like synthetic, bacterial, viral have been used for enhancement of immune response to vaccines. Plant based products are being considered as one option for immune adjuvants.

In one embodiment of the combinatorial composition, vaccine adjuvant composition, vaccine composition or method described, the Dectin-1 agonist is a Dectin 1A or a Dectin 1B.

In one embodiment of the combinatorial composition, vaccine adjuvant composition, vaccine composition or method described, the Dectin-1 agonist includes but is not limited to beta-glucan, heat-killed *Candida albicans*, heat-killed *Saccharomyces cerevisiae*; whole glucan particles (WGP) and Zymosan (cell wall preparation of *S. cerevisiae*).

In some embodiments, the beta-glucan can come from a variety of sources. For example, from *Trametes versicolor, Alcaligenes faecalis, Laminaria digitata, Cetriana islandica, Lasallia pustulana, Sclerotium rolfsii, C. albicans*, and *S. cerevisiae*.

In some embodiments, the dual combination adjuvants are as follows:

| Dectin 1 agonist | TLR4 agonist |
| --- | --- |
| Beta-glucan, | MPLA |
| heat-killed *C. albicans* | MPLA |
| heat-killed *S. cerevisiae* | MPLA |
| WGP | MPLA |
| Zymosan | MPLA |
| Beta-glucan, | GLA |
| heat-killed *C. albicans* | GLA |
| heat-killed *S. cerevisiae* | GLA |
| WGP | GLA |
| Zymosan | GLA |

In other embodiments, triple combination adjuvants are contemplated. For example, MPLA, GLA and Zymosan, or heat-killed *S. cerevisiae*, Zymosan, and MPLA.

In some embodiments, the adjuvant combination contemplated comprises MPLA or GLA with a NK receptor CLR. In one embodiment, the NK receptor CLR is Dectin.

In one embodiment of the vaccine adjuvant composition, vaccine or method described, the at least one TLR7/8 agonist is any agent that would activate the receptor TLR7 and/or TLR8. In some embodiments, the at least one TLR7/8 agonist includes but is not limited to gardiquimod, imiquimod, imidazoquinoline compound R848 (resiquimod), VTX-294, 3M-052, CL087, CL097, and CL075 (INVIVOOGEN™).

In one embodiment of any one of the vaccine adjuvant composition, vaccine or method described, the at least one TLR7/8 agonist is selected from the group consisting of gardiquimod, imiquimod, imidazoquinoline compound R848 (resiquimod), VTX-294, 3M-052, CL087, CL097, and CL075.

CL087 is also known as 9-benzyl-8-hydroxy-2-(2-methoxyethoxy)adenine SM360320, TLR7 Ligand II, 6-Amino-9-benzyl-2-(2-methoxyethoxy)-9H-purin-8-ol, 226907-52-4, and SureCN43700.

CL097 is a highly water-soluble derivative of the imidazoquinoline compound R848. Similarly to R848, CL097 is a TLR7 and TLR8 ligand. In one embodiment, CL097 is 2-(ethoxymethyl)-1 H-imidazo[4,5-c]quinolin-4-amine.

CL075 is also known as 2-propylthiazolo[4,5-c]quinolin-4-amine, CHEMBL512901, 256922-53-9, SureCN482958, CTK0J3836, ANW-67831, CL-075, AKOS016007272, and AK-82105.

In one embodiment of any one of the vaccine adjuvant composition, vaccine or method described, the at least one Mincle agonist includes but is not limited to heat-killed *Mycobacterium tuberculosisis* (HKMT), trehalose-6,6-dibehenate (TDB), Trehalose-6,6-dibehenate formulated with Kolliphor® HS 15 (TDB-HS15), and trehalose-6,6'-dimycolate (TDM).

In one embodiment of any one of the vaccine adjuvant composition, vaccine or method described, the at least one Mincle agonist is selected from a group consisting of HKMT, TDB, TDB-HS15, and TDM.

In some embodiments, the dual combination adjuvants are as follows:

| TLR7/8 agonist | Mincle agonist |
|---|---|
| Gardiquimod | HKMT |
| Imiquimod | HKMT |
| Resiquimod | HKMT |
| CL087 | HKMT |
| CL097 | HKMT |
| CL075 | HKMT |
| VTX-294 | HKMT |
| Gardiquimod | TDB |
| Imiquimod | TDB |
| Resiquimod | TDB |
| CL087 | TDB |
| CL097 | TDB |
| CL075 | TDB |
| VTX-294 | TDB |
| Gardiquimod | TDB-HS15 |
| Imiquimod | TDB-HS15 |
| Resiquimod | TDB-HS15 |
| CL087 | TDB-HS15 |
| CL097 | TDB-HS15 |
| CL075 | TDB-HS15 |
| VTX-294 | TDB-HS15 |
| Gardiquimod | TDM |
| Imiquimod | TDM |
| Resiquimod | TDM |
| CL087 | TDM |
| CL097 | TDM |
| CL075 | TDM |
| VTX-294 | TDM |

In other embodiments, triple combination adjuvants are contemplated. For examples, CL075, TDM, and GLA; CL075, TDM, and MPLA; CL075, TDM, and beta-glucan; and CL075, TDM, and Zymosan.

In one embodiment of any one of the combinatorial composition, vaccine adjuvant composition, vaccine composition or method described, the composition further comprises a pharmaceutically acceptable carrier.

In one embodiment of any one of the vaccine adjuvant composition, vaccine composition or method described, the vaccine adjuvant composition is used in conjunction with a commercial vaccine, e.g., for vaccination purposes.

In one embodiment of any one of the vaccine adjuvant composition, vaccine or method described, the vaccine adjuvant composition is admixed with a commercial vaccine, e.g., for vaccination purposes.

In one embodiment of any one of the vaccine adjuvant composition, vaccine or method described, the commercial vaccine is for vaccination of a childhood disease or infection. For example, the common childhood diseases or infections for which vaccination is typically carried out are measles, mumps, rubella, chicken pox, polio, diphtheria, tetanus, and pertussis.

In one embodiment of any one of the vaccine adjuvant composition, vaccine or method described, the commercial vaccine is for vaccination of a teenager or an adult. For example, Human papillomavirus (HPV), Hepatitis B, HIV and malaria etc.

In one embodiment of any one of the vaccine adjuvant composition, vaccine or method described, the commercial vaccine is for vaccination of seasonal influenza.

In one embodiment of any one of the vaccine composition described, the at least one antigen includes but is not limited to an antigen that is a live attenuated micro-organism that causes known diseases, an antigen that is an inactivated or killed micro-organism that causes known diseases, an antigen that is an inactivated toxin that is produced by a micro-organism that causes known diseases, or an antigen that is a subunit or a conjugate of a subunit of a micro-organism that causes known diseases.

In one embodiment of any one of the vaccine composition described, the micro-organism includes but is not limited to viruses, bacteria, parasitic protists, yeast and fungi. For examples, Respiratory Syncytial Virus (RSV) F protein, RSV pre-fusion (F) protein, RSV Nucleoprotein N, pertussis filamentous hemagglutinin (FHA), a 69-kilodalton outer-membrane protein—pertactin (Pn), and fimbriae (Fim)-types 2 and 3, HIV-GAG, as well as a range of surface proteins derived from Gram-positive or Gram-negative bacteria.

In one embodiment of any one of the vaccine composition described, the at least one antigen includes but is not limited to an antigen against measles, mumps, rubella, chicken pox (Varicella), shingles (Zoster), Influenza (e.g. *Haemophilus influenza* type b), pneumonia (Pneumococcal diseases caused by *Streptococcus pneumoniae*), pneumococcal bacteremia, meningitis (Meningococcal diseases caused by the bacterium, *Neisseria meningitidis*), Rotavirus, diphtheria, tetanus, pertussis (whooping cough), polio (IPV), smallpox, HIV/AIDS, malaria, and Leishmaniasis, Hepatitis A, Hepatitis B, Hepatitis C, Anthrax, Yellow fever, rabies, Human papillomavirus (HPV), *Clostridium tetani* bacterium neurotoxin (tetanospasmin), typhoid, and Japanese encephalitis.

In one embodiment of any one of the vaccine composition described, the at least one antigenis selected from a group consisting of an antigen against measles, mumps, rubella, chicken pox (Varicella), shingles (Zoster), Influenza (e.g. *Haemophilus influenza* type b), pneumonia (Pneumococcal diseases caused by *Streptococcus pneumoniae*), pneumococcal bacteremia, meningitis (Meningococcal diseases caused by the bacterium, *Neisseria meningitidis*), Rotavirus, diphtheria, tetanus, pertussis (whooping cough), polio (IPV), smallpox, HIV/AIDS, malaria, and Leishmaniasis, Hepatitis A, Hepatitis B, Hepatitis C, Anthrax, Yellow fever, rabies, Human papillomavirus (HPV), *Clostridium tetani* bacterium neurotoxin (tetanospasmin), typhoid, and Japanese encephalitis.

In one embodiment of any one of the vaccine composition described, the vaccine adjuvant composition is in an amount of about 85 to 99% of the mass of the vaccine.

In other embodiments of any one of the vaccine composition described, the vaccine adjuvant composition is in an amount of about 86 to 99%, about 87 to 99%, about 88 to 99%, about 89 to 99%, about 90 to 99%, about 91 to 99%, about 92 to 99%, about 93 to 99%, about 94 to 99%, about 95 to 99%, about 96 to 99%, about 94 to 99%, about 95 to 99%, about 96 to 99%, about 97 to 99%, about 98 to 99%, about 85 to 98%, about 85 to 97%, about 85 to 96%, about 85 to 95%, about 85 to 94%, about 85 to 93%, about 85 to 92%, about 85 to 91%, about 85 to 90%, about 85 to 89%, about 85 to 88%, about 85 to 87%, about 85 to 86% of the mass of the vaccine, including all other possible ranges between about 85 to 99% of the mass of the vaccine.

In one embodiment of any one of the vaccine composition or combination adjuvant composition described, the at least TLR4 agonist is in the range of about 0.1 to about 5% of the mass of the fraction.

In one embodiment of any one of the vaccine composition or combination adjuvant composition described, the at least TLR4 agonist is in the range of about 0.1 to about 3% of the mass of the fraction.

In one embodiment of any one of the vaccine composition or combination adjuvant composition described, the at least Dectin-1 agonist is in the range of about 0.1 to about 5% of the mass of the fraction.

In one embodiment of any one of the vaccine composition or combination adjuvant composition described, the at least Dectin-1 agonist is in the range of about 0.1 to about 3% of the mass of the fraction.

In other embodiments, the ranges of any of the disclosed vaccine adjuvant in any one of the vaccine composition or combination adjuvant composition described, e.g., TLR4 agonist, TRL7/8 agonist, TRL7 agonist, TRL8 agonist, Destin-1 agonist, MPLA, GLA, Mincle agonist etc, are about 0.2 to about 5%, about 0.3 to about 5%, about 0.4 to about 5%, about 0.5 to about 5%, about 0.6 to about 5%, about 0.7 to about 5%, about 0.8 to about 5%, about 0.9 to about 5%, about 1 to about 5%, about 1.1 to about 5%, about 1.2 to about 5%, about 1.3 to about 5%, about 1.4 to about 5%, about 1.5 to about 5%, about 1.6 to about 5%, about 1.7 to about 5%, about 1.8 to about 5%, about 1.9 to about 5%, about 2 to about 5%, about 2.1 to about 5%, about 2.2 to about 5%, about 2.3 to about 5%, about 2.4 to about 5%, about 2.5 to about 5%, about 2.6 to about 5%, about 2.7 to about 5%, about 2.8 to about 5%, about 2.9 to about 5%, about 3 to about 5%, about 3.1 to about 5%, about 3.2 to about 5%, about 3.3 to about 5%, about 3.4 to about 5%, about 3.5 to about 5%, about 3.6 to about 5%, about 3.7 to about 5%, about 3.8 to about 5%, about 3.9 to about 5%, about 4 to about 5%, about 4.1 to about 5%, about 4.2 to about 5%, about 4.3 to about 5%, about 4.4 to about 5%, about 4.5 to about 5%, about 4.6 to about 5%, about 4.7 to about 5%, about 4.8 to about 5%, about 4.9 to about 5%, about 0.1 to about 4%, about 0.1 to about 4.1%, about 0.1 to about 4.2%, about 0.1 to about 4.3%, about 0.1 to about 4.4%, about 0.1 to about 4.5%, about 0.1 to about 4.6%, about 0.1 to about 4.7%, about 0.1 to about 4.8%, about 0.1 to about 4.9%, about 0.1 to about 2.9%, about 0.1 to about 3.1%, about 0.1 to about 3.2%, about 0.1 to about 3.3%, about 0.1 to about 3.4%, about 0.1 to about 3.5%, about 0.1 to about 3.6%, about 0.1 to about 3.7%, about 0.1 to about 3.8%, about 0.1 to about 3.9%, about 0.1 to about 1.9%, about 0.1 to about 2%, about 0.1 to about 2.1%, about 0.1 to about 2.2%, about 0.1 to about 2.3%, about 0.1 to about 2.4%, about 0.1 to about 2.5%, about 0.1 to about 2.6%, about 0.1 to about 2.7%, about 0.1 to about 2.8%, about 0.1 to about 0.9%, about 0.1 to about 1%, about 0.1 to about 1.1%, about 0.1 to about 1.2%, about 0.1 to about 1.3%, about 0.1 to about 1.4%, about 0.1 to about 1.5%, about 0.1 to about 1.6%, about 0.1 to about 1.7%, about 0.1 to about 1.8%, %, about 0.1 to about 0.2%, about 0.1 to about 0.3%, about 0.1 to about 0.4%, about 0.1 to about 0.5%, about 0.1 to about 0.6%, about 0.1 to about 0.7%, about 0.1 to about 0.8%, about 0.2 to about 1%, about 0.3 to about 1%, about 0.4 to about 1%, about 0.5 to about 1%, about 0.6 to about 1%, about 0.7 to about 1%, about 0.8 to about 1%, about 0.9 to about 1%, about 0.2 to about 1.5%, about 0.3 to about 1.5%, about 0.4 to about 1.5%, about 0.5 to about 1.5%, about 0.6 to about 1.5%, about 0.7 to about 1.5%, about 0.8 to about 1.5%, about 0.9 to about 1.5%, about 1 to about 1.5%, about 1.2 to about 1.5%, about 1.3 to about 1.5%, about 1.4 to about 1.5%, about 0.2 to about 2%, about 0.3 to about 2%, about 0.4 to about 2%, about 0.5 to about 2%, about 0.6 to about 2%, about 0.7 to about 2%, about 0.8 to about 2%, about 0.9 to about 2%, about 1 to about 2%, about 1.1 to about 2%, about 1.2 to about 2%, about 1.3 to about 2%, about 1.4 to about 2%, about 1.5 to about 2%, about 1.6 to about 2%, about 1.7 to about 2%, about 1.8 to about 2%, about 1.9 to about 2%, about 0.2 to about 2.5%, about 0.3 to about 2.5%, about 0.4 to about 2.5%, about 0.5 to about 2.5%, about 0.6 to about 2.5%, about 0.7 to about 2.5%, about 0.8 to about 2.5%, about 0.9 to about 2.5%, about 1 to about 2.5%, about 1.1 to about 2.5%, about 1.2 to about 2.5%, about 1.3 to about 2.5%, about 1.4 to about 2.5%, about 1.5 to about 2.5%, about 1.6 to about 2.5%, about 1.7 to about 2.5%, about 1.8 to about 2.5%, about 1.9 to about 2.5%, about 2 to about 2.5%, about 2.1 to about 2.5%, about 2.2 to about 2.5%, about 2.3 to about 2.5%, about 2.4 to about 2.5%, about 0.2 to about 3%, about 0.3 to about 3%, about 0.4 to about 3%, about 0.5 to about 3%, about 0.6 to about 3%, about 0.7 to about 3%, about 0.8 to about 3%, about 0.9 to about 3%, about 1 to about 3%, about 1.1 to about 3%, about 1.2 to about 3%, about 1.3 to about 3%, about 1.4 to about 3%, about 1.5 to about 3%, about 1.6 to about 3%, about 1.7 to about 3%, about 1.8 to about 3%, about 1.9 to about 3%, about 2 to about 3%, about 2.1 to about 3%, about 2.2 to about 3%, about 2.3 to about 3%, about 2.4 to about 3%, about 2.5 to about 3%, about 2.6 to about 3%, about 2.7 to about 3%, about 2.8 to about 3%, about 2.9 to about 3%, about 0.1 to about 2.9%, about 0.2 to about 2.9%, about 0.3 to about 2.9%, about 0.4 to about 2.9%, about 0.5 to about 2.9%, about 0.6 to about 2.9%, about 0.7 to about 2.9%, about 0.8 to about 2.9%, about 0.9 to about 2.9%, about 1 to about 2.9%, about 1.1 to about 2.9%, about 1.2 to about 2.9%, about 1.3 to about 2.9%, about 1.4 to about 2.9%, about 1.5 to about 2.9%, about 1.6 to about 2.9%, about 1.7 to about 2.9%, about 1.8 to about 2.9%, about 1.9 to about 2.9%, about 2 to about 2.9%, about 2.1 to about 2.9%, about 2.2 to about 2.9%, about 2.3 to about 2.9%, about 2.4 to about 2.9%, about 2.5 to about 2.9%, about 2.6 to about 2.9%, about 2.7 to about 2.9%, about 2.8 to about 2.9%, about 0.1 to about 2.7%, about 0.2 to about 2.7%, about 0.3 to about 2.7%, about 0.4 to about 2.7%, about 0.5 to about 2.7%, about 0.6 to about 2.7%, about 0.7 to about 2.7%, about 0.8 to about 2.7%, about 0.9 to about 2.7%, about 1 to about 2.7%, about 1.1 to about 2.7%, about 1.2 to about 2.7%, about 1.3 to about 2.7%, about 1.4 to about 2.7%, about 1.5 to about 2.7%, about 1.6 to about 2.7%, about 1.7 to about 2.7%, about 1.8 to about 2.7%, about 1.9 to about 2.7%, about 2 to about 2.7%, about 2.1 to about 2.7%, about 2.2 to about 2.7%, about 2.3 to about 2.7%, about 2.4 to about 2.7%, about 2.5 to about 2.7%, about 2.6 to about 2.7%, about 0.1 to about 2.5%, about 0.2 to about 2.5%, about 0.3 to about 2.5%, about 0.4 to about 2.5%, about 0.5 to about 2.5%, about 0.6 to about 2.5%, about 0.7 to about 2.5%, about 0.8 to about 2.9%, about 0.9 to about 2.5%, about 1 to about 2.9%, about 1.1 to about 2.5%, about 1.2 to about 2.5%, about 1.3 to about 2.5%, about 1.4 to about 2.5%, about 1.5 to about 2.5%, about 1.6 to about 2.5%, about 1.7 to about 2.5%, about 1.8 to about 2.5%, about 1.9 to about 2.5%, about 2 to about 2.5%, about 2.1 to about 2.5%, about 2.2 to about 2.5%, about 2.3 to about 2.5%, about 2.4 to about 2.5%, about 0.1 to about 2.3%, about 0.2 to about 2.3%, about 0.3 to about 2.3%, about 0.4 to about 2.3%, about 0.5 to about 2.3%, about 0.6 to about 2.3%, about 0.7 to about 2.3%, about 0.8 to about 2.3%, about 0.9 to about 2.3%, about 1 to about 2.3%, about 1.1 to about 2.3%, about 1.2 to about 2.3%, about 1.3 to about 2.3%, about 1.4 to about 2.3%, about 1.5 to about 2.3%, about 1.6 to about 2.3%, about 1.7 to about 2.3%, about 1.8 to about 2.3%, about 1.9 to about 2.3%, about 2 to about 2.3%, about 2.1 to about 2.9%, about 2.2 to about 2.3%, about 0.1 to about 2.1%, about 0.2 to about 2.9%, about 0.3 to about 2.1%, about 0.4 to about 2.1%, about 0.5 to about 2.1%, about 0.6 to about 2.1%, about 0.7 to about 2.1%, about 0.8 to about 2.1%, about 0.9 to about 2.1%, about 1 to about 2.1%, about 1.1 to about 2.1%, about 1.2 to about 2.1%, about 1.3 to about 2.1%, about 1.4 to about 2.1%, about 1.5 to about 2.1%, about 1.6 to about 2.1%, about 1.7 to about 2.1%, about 1.8 to about 2.1%, about 1.9 to about 2.1%, about 2 to about 2.1%, about 0.1 to about 3.5%, about 0.2 to about 3.5%, about 0.3 to about 3.5%, about 0.4 to about 3.5%, about 0.5 to about 3.5%, about 0.6 to about 3.5%, about 0.7 to about 3.5%, about 0.8 to about 3.5%, about 0.9 to about 3.5%, about 1 to about 3.5%, about 1.1 to about 3.5%, about 1.2 to about 3.5%, about 1.3 to about 3.5%, about 1.4 to about 3.5%, about 1.5 to about 3.5%, about 1.6 to about 3.5%, about 1.7 to about 3.5%, about 1.8 to about 3.5%, about 1.9 to about 3.5%, about 2 to about 3.5%, about 2.1 to about 3.5%, about 2.2 to about 3.5%, about 2.3 to about 3.5%, about 2.4 to about 3.5%, about 2.5 to about 3.5%, about 2.6 to about 3.5%, about 2.7 to about 3.5%, about 2.8 to about 3.5%, about 2.9 to about 3.5%, about 3 to about 3.5%, about 3.1 to about 3.5%, about 3.2 to about 3.5%, about 3.3 to about 3.5%, about 3.4 to about 3.5%, about 0.2 to about 4%, about 0.3 to about 4%, about 0.4 to about 4%, about 0.5 to about 4%, about 0.6 to about 4%, about 0.7 to about 4%, about 0.8 to about 4%, about 0.9 to about 4%, about 1 to about 4%, about 1.1 to about 4%, about 1.2 to about 4%, about 1.3 to about 4%, about 1.4 to about 4%, about 1.5 to about 4%, about 1.6 to about 4%, about 1.7 to about 4%, about 1.8 to about 4%, about 1.9 to about 4%, about 2 to about 4%, about 2.1 to about 4%, about 2.2 to about 4%, about 2.3 to about 4%, about 2.4 to about 4%, about 2.5 to about 4%, about 2.6 to about 4%, about 2.7 to about 4%, about 2.8 to about 4%, about 2.9 to about 4%, about 3 to about 4%, about 3.1 to about 5%, about 3.2 to about 4%, about 3.3 to about 4%, about 3.4 to about 4%, about 3.5 to about 4%, about 3.6 to about 4%, about 3.7 to about 4%, about 3.8 to about 4%, about 3.9 to about 4%, about 0.2 to about 4.5%, about 0.3 to about 4.5%, about 0.4 to about 4.5%, about 0.5 to about 4.5%, about 0.6 to about 4.5%, about 0.7 to about 4.5%, about 0.8 to about 4.5%, about 0.9 to about 4.5%, about 1 to about 4.5%, about 1.1 to about 4.5%, about 1.2 to about 4.5%, about 1.3 to about 4.5%, about 1.4 to about 4.5%, about 1.5 to about 4.5%, about 1.6 to about 4.5%, about 1.7 to about 4.5%, about 1.8 to about 4.5%, about 1.9 to about 4.5%, about 2 to about 4.5%, about 2.1 to about 4.5%, about 2.2 to about 4.5%, about 2.3 to about 4.5%, about 2.4 to about 4%, about 2.5 to about 4.5%, about 2.6 to about 4.5%, about 2.7 to about 4.5%, about 2.8 to about 4.5%, about 2.9 to about 4.5%, about 3 to about 4.5%, about 3.1 to about 4.5%, about 3.2 to about 4.5%, about 3.3 to about 4.5%, about 3.4 to about 4.5%, about 3.5 to about 4.5%, about 3.6 to about 4.5%, about 3.7 to about 4.5%, about 3.8 to about 4.5%, about 3.9 to about 4.5%, about 4 to about 4.5%, about 4.1 to about 4.5%, about 4.2 to about 4.5%, about 4.3 to about 4.5%, about 4.4 to about 4.5%, including all other possible ranges between 0.1 to 5% of the mass of the fraction.

In one embodiment of any one of the vaccine composition described, the vaccine composition further comprises alum-hydroxide as a co-adjuvant.

In one embodiment of any one of the vaccine composition described, the concentration of the adjuvant composition is about 150 µg per single dose.

In other embodiments of any one of the vaccine composition described, the concentration of the adjuvant composition is about 50 µg, 60 µg, 70 µg, 80 µg, 90 µg, 100 µg, 110 µg, 120 µg, 130 µg, 140 µg, 160 µg, 170 µg, 180 µg, 190 µg, 200 µg, 210 µg, 220 µg, 230 µg, 240 µg, 250 µg, 260 µg, 270 µg, 280 µg, 290 µg, 300 µg, 310 µg, 320 µg, 330 µg, 340 µg, 350 µg, 360 µg, 370 µg, 380 µg, 390 µg, 400 µg, 410 µg, 420 µg, 430 µg, 440 µg, 450 µg, 460 µg, 470 µg, 480 µg, 490 µg, 500 µg per single dose.

In one embodiment of any one of the vaccine composition described, the concentration of the adjuvant composition is about 150 µg to about 150 mg/single dose.

In other embodiments of any one of the vaccine composition described, the concentration of the adjuvant composition is about 150 µg to about 150 mg, 160 µg to about 150 mg, 170 µg to about 150 mg, 180 µg to about 150 mg, 190 µg to about 150 mg, 200 µg to about 150 mg, 210 µg to about 150 mg, 220 µg to about 150 mg, 230 µg to about 150 mg, 240 µg to about 150 mg, 250 µg to about 150 mg, 260 µg to about 150 mg, 270 µg to about 150 mg, 280 µg to about 150 mg, 290 µg to about 150 mg, 300 µg to about 150 mg, 310 µg to about 150 mg, 350 µg to about 150 mg, 400 µg to about 150 mg, 450 µg to about 150 mg, 500 µg to about 150 mg, 550 µg to about 150 mg, 600 µg to about 150 mg, 650 µg to about 150 mg, 700 µg to about 150 mg, 750 µg to about 150 mg, 800 µg to about 150 mg, 850 µg to about 150 mg, 900 µg to about 150 mg, 950 µg to about 150 mg, 1000 µg to about 150 mg per dose, 150 µg to about 100 mg, 160 µg to about 100 mg, 170 µg to about 100 mg, 180 µg to about 100 mg, 190 µg to about 100 mg, 200 µg to about 100 mg, 210 µg to about 100 mg, 220 µg to about 100 mg, 230 µg to about 100 mg, 240 µg to about 100 mg, 250 µg to about 100 mg, 260 µg to about 100 mg, 270 µg to about 100 mg, 280 µg to about 100 mg, 290 µg to about 100 mg, 300 µg to about 100 mg, 310 µg to about 100 mg, 350 µg to about 100 mg, 400 µg to about 100 mg, 450 µg to about 100 mg, 500 µg to about 100 mg, 550 µg to about 100 mg, 600 µg to about 100 mg, 650 µg to about 100 mg, 700 µg to about 100 mg, 750 µg to about 100 mg, 800 µg to about 100 mg, 850 µg to about 100 mg, 900 µg to about 100 mg, 950 µg to about 100 mg, 1000 µg to about 100 mg per dose, 150 µg to about 50 mg, 160 µg to about 50 mg, 170 µg to about 50 mg, 180 µg to about 50 mg, 190 µg to about 50 mg, 200 µg to about 50 mg, 210 µg to about 50 mg, 220 µg to about 50 mg, 230 µg to about 50 mg, 240 µg to about 50 mg, 250 µg to about 50 mg, 260 µg to about 50 mg, 270 µg to about 50 mg, 280 µg to about 50 mg, 290 µg to about 50 mg, 300 µg to about 50 mg, 310 µg to about 50 mg, 350 µg to about 50 mg, 400 µg to about 50 mg, 450 µg to about 50 mg, 500 µg to about 50 mg, 550 µg to about 50 mg, 600 µg to about 50 mg, 650 µg to about 50 mg, 700 µg to about 50 mg, 750 µg to about 50 mg, 800 µg to about 50 mg, 850 µg to about 50 mg, 900 µg to about 50 mg, 950 µg to about 50 mg, 1000 µg to about 50 mg per dose, 150 µg to about 10 mg, 160 µg to about 10 mg, 170 µg to about 10 mg, 180 µg to about 10 mg, 190 µg to about 10 mg, 200 µg to about 10 mg, 210 µg to about 10 mg, 220 µg to about 10 mg, 230 µg to about 10 mg, 240 µg to about 10 mg, 250 µg to about 10 mg, 260 µg to about 10 mg, 270 µg to about 10 mg, 280 µg to about 10 mg, 290 µg to about 10 mg, 300 µg to about 10 mg, 310 µg to about 10 mg, 350 µg to about 10 mg, 400 µg to about 10 mg, 450 µg to about 10 mg, 500 µg to about 10 mg, 550 µg to about 10 mg, 600 µg to about 10 mg, 650 µg to about 10 mg, 700 µg to about 10 mg, 750 µg to about 10 mg, 800 µg to about 10 mg, 850 µg to about 10 mg, 900 µg to about 10 mg, 950 µg to about 10 mg, 1000 µg to about 10 mg per dose, 150 µg to about 5 mg, 160 µg to about 5 mg, 170 µg to about 5 mg, 180 µg to about 5 mg, 190 µg to about 5 mg, 200 µg to about 5 mg, 210 µg to about 5 mg, 220 µg to about 5 mg, 230 µg to about 5 mg, 240 µg to about 5 mg, 250 µg to about 5 mg, 260 µg to about 5 mg, 270 µg to about 5 mg, 280 µg to about 5 mg, 290 µg to about 5 mg, 300 µg to about 5 mg, 310 µg to about 5 mg, 350 µg to about 5 mg, 400 µg to about 5 mg, 450 µg to about 5 mg, 500 µg to about 5 mg, 550 µg to about 5 mg, 600 µg to about 5 mg, 650 µg to about 5 mg, 700 µg to about 5 mg, 750 µg to about 5 mg, 800 µg to about 5 mg, 850 µg to about 5 mg, 900 µg to about 5 mg, 950 µg to about 5 mg, 1000 µg to about 5 mg, 1050 µg to about 5 mg, 1500 µg to about 5 mg, 2000 µg to about 5 mg, 2500 µg to about 5 mg, 3000 µg to about 5 mg, 3500 µg to about 5 mg, 4000 µg to about 5 mg, 4500 µg to about 5 mg, 150 µg to about 1 mg, 160 µg to about 1 mg, 170 µg to about 1 mg, 180 µg to about 1 mg, 190 µg to about 1 mg, 200 µg to about 1 mg, 210 µg to about 1 mg, 220 µg to about 1 mg, 230 µg to about 1 mg, 240 µg to about 1 mg, 250 µg to about 1 mg, 260 µg to about 1 mg, 270 µg to about 1 mg, 280 µg to about 1 mg, 290 µg to about 1 mg, 300 µg to about 1 mg, 310 µg to about 1 mg, 350 µg to about 1 mg, 400 µg to about 1 mg, 450 µg to about 1 mg, 500 µg to about 1 mg, 550 µg to about 1 mg, 600 µg to about 1 mg, 650 µg to about 1 mg, 700 µg to about 1 mg, 750 µg to about 1 mg, 800 µg to about 1 mg, 850 µg to about 1 mg, 900 µg to about 1 mg, 950 µg to about 1 mg, and including all other possible ranges between 150 µg to 150 mg per dose.

In one embodiment of any one of the vaccine composition or combination adjuvant composition described, the concentration of TDB is about 10-100 microgram/ml. In other embodiments, the concentration of TDB is about 10-90, 10-80, 10-70, 10-60, 10-50, 10-55, 10-40, 10-45, 10-30, 10-25, 10-20, 20-100, 25-100, 30-100, 35-100, 40-100, 45-100, 50-100, 55-100, 60-100, 70-100, 80-100, 90-100, 20-90, 20-80, 20-70, 20-60, 20-50, 20-40, 20-30, 30-90, 30-80, 30-70, 30-60, 30-50, 30-40, 40-90, 40-80, 40-70, 40-60, 40-50, 50-90, 50-80, 50-70, 50-60, 60-90, 60-80, 60-70, 70-90, 70-80 µg/ml including all other intermediate ranges between 10-100 µg/ml.

In one embodiment of any one of the vaccine composition or combination adjuvant composition described, the concentration of R848 is about 1-50 micromolar. In other embodiments, the concentration of R848 is about 5-50, 10-50, 15-50, 20-50, 25-50, 30-50, 35-50, 40-50, 45-50, 1-45, 5-45, 10-45, 15-45, 20-45, 25-45, 30-45, 35-45, 40-45, 10-40, 10-30, 10-20, 15-40, 15-45, 15-30, 15-35, 15-20, 15-25, 20-40, 20-35, 20-30, 20-25, 25-40, 25-35, 35-30 µM, including all other intermediate ranges between 1-50 µM.

In one embodiment of any one of the vaccine composition or combination adjuvant composition described, the concentration of Zymosan (Dectin) is about 10-100 microgram/ml. In other embodiments, the concentration of Dectin is about 10-90, 10-80, 10-70, 10-60, 10-50, 10-55, 10-40, 10-45, 10-30, 10-25, 10-20, 20-100, 25-100, 30-100, 35-100, 40-100, 45-100, 50-100, 55-100, 60-100, 70-100, 80-100, 90-100, 20-90, 20-80, 20-70, 20-60, 20-50, 20-40, 20-30, 30-90, 30-80, 30-70, 30-60, 30-50, 30-40, 40-90, 40-80, 40-70, 40-60, 40-50, 50-90, 50-80, 50-70, 50-60, 60-90, 60-80, 60-70, 70-90, 70-80 µg/ml including all other intermediate ranges between 10-100 µg/ml.

In one embodiment of any one of the vaccine composition or combination adjuvant composition described, the concentration of MPLA or GLA is about 100 nanogram/ml-1 microgram/ml. In other embodiments, the concentration of MPLA or GLA is about 0.2-1, 0.3-1, 0.4-1, 0.5-1, 0.6-1, 0.7-1, 0.8-1, 0.9-1, 0.1-0.9, 0.1-0.8, 0.1-0.7, 0.1-0.6, 0.1-0.5, 0.1-0.4, 0.1-0.3, 0.1-0.2, 0.2-0.9, 0.2-0.8, 0.2-0.7, 0.2-0.6, 0.2-0.5, 0.2-0.4, 0.2-0.3, 0.3-0.9, 0.3-0.8, 0.3-0.7, 0.3-0.6, 0.3-0.5, 0.3-0.4, 0.4-0.9, 0.4-0.8, 0.4-0.7, 0.4-0.6, 0.4-0.5, 0.5-0.9, 0.5-0.8, 0.5-0.7, 0.5-0.6, 0.6-0.9, 0.6-0.8, 0.6-0.7, 0.7-0.9, 0.7-0.8, 0.8-0.9 µg/ml including all other intermediate ranges to the second decimal place between 0.1-1 µg/ml.

In other embodiments, the ranges of any of the disclosed vaccine adjuvant in any one of the vaccine composition or combination adjuvant composition described, e.g., TLR4 agonist, TRL7/8 agonist, TRL7 agonist, TRL8 agonist, Destin-1 agonist, MPLA, GLA, Mincle agonist etc, are about 10-100 µg/ml, 10-90, 10-80, 10-70, 10-60, 10-50, 10-55, 10-40, 10-45, 10-30, 10-25, 10-20, 20-100, 25-100, 30-100, 35-100, 40-100, 45-100, 50-100, 55-100, 60-100, 70-100, 80-100, 90-100, 20-90, 20-80, 20-70, 20-60, 20-50, 20-40, 20-30, 30-90, 30-80, 30-70, 30-60, 30-50, 30-40, 40-90, 40-80, 40-70, 40-60, 40-50, 50-90, 50-80, 50-70, 50-60, 60-90, 60-80, 60-70, 70-90, 70-80 µg/ml, about 1-50 µM, 5-50, 10-50, 15-50, 20-50, 25-50, 30-50, 35-50, 40-50, 45-50, 1-45, 5-45, 10-45, 15-45, 20-45, 25-45, 30-45, 35-45, 40-45, 10-40, 10-30, 10-20, 15-40, 15-45, 15-30, 15-35, 15-20, 15-25, 20-40, 20-35, 20-30, 20-25, 25-40, 25-35, 35-30 µM, about 0.1-1 µg/ml, 0.2-1, 0.3-1, 0.4-1, 0.5-1, 0.6-1, 0.7-1, 0.8-1, 0.9-1, 0.1-0.9, 0.1-0.8, 0.1-0.7, 0.1-0.6, 0.1-0.5, 0.1-0.4, 0.1-0.3, 0.1-0.2, 0.2-0.9, 0.2-0.8, 0.2-0.7, 0.2-0.6, 0.2-0.5, 0.2-0.4, 0.2-0.3, 0.3-0.9, 0.3-0.8, 0.3-0.7, 0.3-0.6, 0.3-0.5, 0.3-0.4, 0.4-0.9, 0.4-0.8, 0.4-0.7, 0.4-0.6, 0.4-0.5, 0.5-0.9, 0.5-0.8, 0.5-0.7, 0.5-0.6, 0.6-0.9, 0.6-0.8, 0.6-0.7, 0.7-0.9, 0.7-0.8, or 0.8-0.9 µg/ml.

In one embodiment of any one of the vaccine composition or combination adjuvant composition described, the composition is formulated in an oil-in-water emulsion. In another embodiment, the composition is formulated as a nanoparticle, such as a polymersome or a liposome. Methods of making such formulation are known in the art, for example, see U.S. Pat. Nos. 6,225,198 5,505,928, 7,253,119 and 8,414,926, the contents are incorporated by reference in their entirety.

In one embodiment of any one of the methods described, the subject is a mammal. In other embodiments of any one of the methods described herein, the subject is a newborn, an infant, an elderly subject, or a subject who is in need of enhancing the immune system. For example, in a subject who is immune compromise, a subject who has weakened immune system or response, a subject who is diabetic, or a subject who has a defect in the immune system.

In one embodiment of any one of the methods or compositions or uses described, the subject is a mammal with an immune system. In one embodiment, the subject is a newborn or an infant. In another embodiment, the subject is a human child under the age 12 years old. In another embodiment, the subject is a human adolescent under the age 21 years old. In another embodiment, the subject is a human adult over the age 21 years old. In another embodiment, the subject is a human adult over the age 65 years old, an elderly human adult.

In one embodiment, the subject is an immune compromised mammal having an immune system. As used here, in one embodiment, the immune compromised means having an impaired immune system. A person who has an immunodeficiency of any kind is said to be immunocompromised. Immunodeficiency (or immune deficiency) is a state in which the immune system's ability to fight infectious disease is compromised or entirely absent. Immunodeficiency may also decrease cancer immunosurveillance. Most cases of immunodeficiency are acquired ("secondary") but some people are born with defects in their immune system, or primary immunodeficiency. Transplant patients take medications to suppress their immune system as an anti-rejection measure, as do some patients suffering from an over-active immune system. A person who has an immunodeficiency of any kind is said to be immunocompromised. An immunocompromised person may be particularly vulnerable to opportunistic infections, in addition to normal infections that could affect everyone. Causes of immune deficiency include but are not limited to bone marrow and other transplantation, AIDS, rancer and other chemotherapy, diabetes, lymphoma, glucocorticoid therapy, dysfunction, such as chronic granulomatous disease, multiple myeloma, chronic lymphoid leukemia, splenectomy, trauma and sickle-cell anemia.

In one embodiment of any one of the methods described, the mammal is a human.

In another embodiment of any one of the method described, the human mammal is a human adult.

In another embodiment of any one of the method described, the human mammal is a human newborn.

In another embodiment of any one of the method described, the subject is a non-human mammal.

In one embodiment of any one of the method described, there is at induction of Th1-polarizing cytokines in the subject upon the administering the vaccine adjuvant described. The cytokines can be determined by any method known in the art, for example, as described in the Examples section.

In one embodiment of any one of the method described, the Th1-polarizing cytokines are TNF-α, IFN-γ and/or the T-helper 17 (Th17)-polarizing cytokine IL-1β.

In one embodiment of any one of the method described, there is an induction of IFN-γ cytokine in the subject upon the administration of the combinatorial composition or vaccine adjuvant composition described.

In one embodiment of any one of the method described, there is an induction of TNF-α cytokine in the subject upon the administration of the combinatorial composition or vaccine adjuvant composition described.

In one embodiment of any one of the method described, there is an induction of IL-1β cytokine in the subject upon the administration of the combinatorial composition or vaccine adjuvant composition described.

In one embodiment of any one of the method described, there is an induction of IL-12p70 cytokine in the subject upon the administration of the combinatorial composition or vaccine adjuvant composition described.

In one embodiment of any one of the method described, there is an induction of inducing differentiation of naïve T cells to differentiate into IFN-γ-producing T cells cytokine in the subject upon the administration of the combinatorial composition or vaccine adjuvant composition described.

In one embodiment of any one of the method described, there is an enhanced synergistic activation of the NF-kB and NLRP3 inflammasome pathways in the subject upon the administration of the combinatorial composition or vaccine adjuvant composition described.

In one embodiment of any one of the method of inducing the production of Th1-polarizing cytokines, IFN-γ and/or IL-12p70 cytokines in dendritic cells, the Th1-polarizing cytokines are TNF-α, IFN-γ and/or the T-helper 17 (Th17)-polarizing cytokine IL-1β.

In one embodiment of any one of the method of inducing the production of Th1-polarizing cytokines, IFN-γ and/or IL-12p70 cytokines in dendritic cells, the dendritic cells are immature dendritic cells.

In one embodiment of any one of the method of inducing the production of Th1-polarizing cytokines, IFN-γ and/or IL-12p70 cytokines in dendritic cells, the dendritic cells are adult DCs, newborn DCs, or infant DCs.

In one embodiment of any one of the method of inducing the production of Th1-polarizing cytokines, IFN-γ and/or IL-12p70 cytokines in dendritic cells, the contacting is in vivo, ex vivo or in vitro.

In one embodiment of any one of the method of inducing the production of Th1-polarizing cytokines, IFN-γ and/or IL-12p70 cytokines in dendritic cells, the in vivo in the subject.

In one embodiment of any one of the method of inducing the production of Th1-polarizing cytokines, IFN-γ and/or IL-12p70 cytokines in dendritic cells, the method further comprises isolating the DCs.

In one embodiment of any one of the method of inducing the production of Th1-polarizing cytokines, IFN-γ and/or IL-12p70 cytokines in dendritic cells, the method further comprises providing a population of the DCs. In one embodiment, the isolated population of DCs is obtained from a subject.

In one embodiment of any one of the method described, the naïve T cells are CD4+ and/or CD45RA+ and/or CD45RO−.

Formulation and Application

In one embodiment, the combinatorial composition, combination vaccine adjuvant or the vaccine compositions described herein comprise a pharmaceutically acceptable carrier. In another embodiment, the vaccine composition described herein is formulated for administering to a mammal. Suitable formulations can be found in Remington's Pharmaceutical Sciences, 16th and 18th Eds., Mack Publishing, Easton, Pa. (1980 and 1990), and Introduction to Pharmaceutical Dosage Forms, 4th Edition, Lea & Febiger, Philadelphia (1985), each of which is incorporated herein by reference.

In one embodiment, the combinatorial composition, combination vaccine adjuvant or the vaccine compositions described herein comprise pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. For all administrations, conventional depot forms are suitably used. Such forms include, for example, microcapsules, nano-capsules, polymersomes, liposomes, plasters, inhalation forms, nose sprays, sublingual tablets, and sustained release preparations. For examples of sustained release compositions, see U.S. Pat. Nos. 3,773,919, 3,887,699, EP 58,481A, EP 158,277A, Canadian Patent No. 1176565; U. Sidman et al., Biopolymers 22:547 (1983) and R. Langer et al., Chem. Tech. 12:98 (1982). The proteins will usually be formulated at a concentration of about 0.1 mg/ml to 100 mg/ml per application per patient.

In one embodiment, other ingredients can be added to the combinatorial composition, combination vaccine adjuvant or the vaccine composition or formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In one embodiment, any one of the combinatorial composition, combination vaccine adjuvant or the vaccine composition is formulated to comprise liposomes or nanoparticles. In one embodiment of any one of the combination vaccine adjuvant or the vaccine composition are formulated as an emulsion.

In one embodiment of any one of the combinatorial composition, combination vaccine adjuvant or the vaccine compositions described herein for administration must be sterile. Sterility is readily accomplished by filtration through sterile filtration membranes (e.g., 0.2 micron membranes).

In some embodiments, the combinatorial composition, combination vaccine adjuvant or the vaccine composition described herein further comprises pharmaceutical excipients including, but not limited to biocompatible oils, physiological saline solutions, preservatives, carbohydrate, protein, amino acids, osmotic pressure controlling agents, carrier gases, pH-controlling agents, organic solvents, hydrophobic agents, enzyme inhibitors, water absorbing polymers, surfactants, absorption promoters and anti-oxidative agents. Representative examples of carbohydrates include soluble sugars such as hydropropyl cellulose, carboxymethyl cellulose, sodium carboxyl cellulose, hyaluronic acid, chitosan, alginate, glucose, xylose, galactose, fructose, maltose, saccharose, dextran, chondroitin sulfate, etc. Representative examples of proteins include albumin, gelatin, etc. Representative examples of amino acids include glycine, alanine, glutamic acid, arginine, lysine, and their salts.

The formulations of the combinatorial composition, combination vaccine adjuvant or the vaccine compositions can incorporate a stabilizer. Illustrative stabilizers are polyethylene glycol, proteins, saccharide, amino acids, inorganic acids, and organic acids thatov may be used either on their own or as admixtures. Two or more stabilizers may be used in aqueous solutions at the appropriate concentration and/or pH. The specific osmotic pressure in such aqueous solution is generally in the range of 0.1-3.0 osmoses, preferably in the range of 0.80-1.2. The pH of the aqueous solution is adjusted to be within the range of 5.0-9.0, preferably within the range of 6-8.

When oral preparations are desired, the combination vaccine adjuvant or the vaccine compositions can be combined with typical carriers, such as lactose, sucrose, starch, talc magnesium stearate, crystalline cellulose, methyl cellulose, carboxymethyl cellulose, glycerin, sodium alginate or gum arabic among others.

In some embodiments, the combinatorial composition, combination vaccine adjuvant or the vaccine compositions described herein can be administered systemically, intravenously, intranasally, intramuscularly, subcutaneously, infraperitoneally or orally. A preferred route of administration is oral, intranasal or intramuscular.

In another embodiment, for example, in the treatment of infection, the combinatorial composition described herein is administered directly to the site or location of infection, e.g., into a wound. In another embodiment, the combinatorial composition described herein incorporated into wound dressing materials which are applied onto wounds in order to treat the infection therein.

Vaccination can be conducted by conventional methods. For example, a polypeptide can be used in a suitable diluent such as saline or water, or complete or incomplete adjuvants. The vaccine can be administered by any route appropriate for eliciting an immune response. The vaccine can be administered once or at periodic intervals until an immune response is elicited. Immune responses can be detected by a variety of methods known to those skilled in the art, including but not limited to, antibody production, cytotoxicity assay, proliferation assay and cytokine release assays. For example, samples of blood can be drawn from the immunized mammal and analyzed for the presence of antibodies against the antigen administered in the respective vaccine and the titer of these antibodies can be determined by methods known in the art.

The precise dose to be employed in the formulation will also depend on the route of administration and should be decided according to the judgment of the practitioner and each patient's circumstances. For example, a range of 25 µg-900 mg total antigens can be administered depending on the route of immunization.

In one embodiment, the combination adjuvant composition is administered first followed by the vaccine or antigen.

In another embodiment, the combination adjuvant composition is administered after the vaccine or antigen.

In another embodiment, the combination adjuvant composition is administered simultaneously with the vaccine or antigen.

In another embodiment, the combination adjuvant composition is admixed together with the vaccine or antigen and then administered simultaneously.

The present invention can be defined in any of the following numbered paragraphs:

[1] A combinatorial composition comprising at least one TLR4 agonist and at least one Dectin-1 agonist, wherein the at least TLR4 agonist is selected from monophosphoryl lipid A (MPLA) or glycopyranosyl lipid A (GLA).

[2] A combinatorial composition comprising at least one TLR7/8 agonist and at least one Mincle agonist.

[3] The combinatorial composition of paragraph 1, the composition further comprising at least one TLR7/8 agonist and/or at least one Mincle agonist.

[4] The combinatorial composition of paragraph 2, the composition further comprising at least one TLR4 agonist and at least one Dectin-1 agonist, wherein the at least TLR4 agonist is selected from monophosphoryl lipid A (MPLA) or glycopyranosyl lipid A (GLA).

[5] The combinatorial composition of paragraph 2 or 3, wherein the at least one TLR7/8 agonist is selected from the group consisting of gardiquimod, imiquimod, imidazoquinoline compound R848 (resiquimod), CL087, CL097, and CL075.

[6] The combinatorial composition of paragraph 2, 3 or 4, wherein the at least one Mincle agonist is selected from a group consisting of Trehalose-6,6-dibehenate (TDB), HKMT, TDB-HS15, and TDM.

[7] The combinatorial composition of any one of paragraphs 1-6 further comprising a pharmaceutically acceptable carrier.

[8] A vaccine composition comprising at least one antigen and a combinatorial composition of any one of paragraphs 1-6.

[9] The vaccine composition of paragraph 6, further comprising a pharmaceutically acceptable carrier.

[10] The vaccine composition of paragraph 8 or 9, wherein the at least one antigen is selected from a group consisting of an antigen that is a live attenuated micro-organism that causes known diseases, an antigen that is an inactivated or killed micro-organism that causes known diseases, an antigen that is an inactivated toxin that is produced by a micro-organism that causes known diseases, or an antigen that is a subunit or a conjugate of a subunit of a micro-organism that causes known diseases.

[11] The vaccine composition of paragraph 8, 9 or 10, wherein vaccine adjuvant composition is in an amount of about 85 to 99% of the mass of the vaccine.

[12] The vaccine composition of any one of paragraphs 8-11, wherein the at least TLR4 agonist is in the range of about 0.1 to about 5% of the mass of the fraction.

[13] The vaccine composition of any one of paragraphs 8-11, wherein the at least TLR4 agonist is in the range of about 0.1 to about 3% of the mass of the fraction.

[14] The vaccine composition of any one of paragraphs 8-13, wherein the at least Dectin-1 agonist is in the range of about 0.1 to about 5% of the mass of the fraction.

[15] The vaccine composition of any one of paragraphs 8-13, wherein the at least Dectin-1 agonist is in the range of about 0.1 to about 3% of the mass of the fraction.

[16] The vaccine composition of any one of paragraphs 8-15 further comprising alum-hydroxide as a co-adjuvant.

[17] The vaccine composition of any one of paragraphs 8-16, wherein the concentration of the adjuvant composition is about 150 µg to 150 mg/single dose.

[18] The vaccine composition of any one of paragraph 8-17, wherein the vaccine is formulated in an oil-in-water emulsion.

[19] A method of enhancing an immune response to an antigen in a subject comprising administering a combinatorial composition comprising at least one TLR4 agonist and at least one Dectin-1A agonist with the antigen, wherein the at least TLR4 agonist is selected from monophosphoryl lipid A (MPLA) or glycopyranosyl lipid A (GLA).

[20] A method of enhancing an immune response to an antigen in a subject comprising administering a vaccine adjuvant composition comprising at least one TLR7/8 agonist and at least one Mincle agonist with the antigen.

[21] The method of paragraph 19, wherein the at least one TLR7/8 agonist is selected from imidazoquinoline compound R848, gardiquimod, imiquimod, imidazoquinoline compound R848 (resiquimod), CL087, CL097, 3M-052, single stranded RNAs (ssRNAs), 3M-052, benzazepine TLR8 agonist compounds such as VentiRx (VTX)-294, and CL075.

[22] The method of paragraph 19 or 20, wherein the at least one Mincle agonist is selected from a group consisting of Trehalose-6,6-dibehenate (TDB), *Mycobacterium tuberculosis* (HKMT), Trehalose-6,6-dibehenate formulated with Kolliphor® HS 15 (TDB-HS15), and trehalose-6,6'-dimycolate (TDM).

[23] The method of any one of paragraph 19-22, wherein the subject is a human or human newborn or a non-human mammal.

[24] Use of at least one TLR4 agonist and at least one Dectin-1 agonist for the manufacture of a combination adjuvant wherein the at least TLR4 agonist is selected from monophosphoryl lipid A (MPLA) or glycopyranosyl lipid A (GLA).

[25] Use of at least one TLR7/8 agonist and at least one Mincle agonist for the manufacture of a vaccine composition.

[26] Use of at least one TLR4 agonist and at least one Dectin-1 agonist for the manufacture of a vaccine composition wherein the at least TLR4 agonist is selected from monophosphoryl lipid A (MPLA) or glycopyranosyl lipid A (GLA).

[27] Use of at least one TLR7/8 agonist and at least one Mincle agonist for the manufacture of a combination adjuvant.

[28] Use of at least one TLR4 agonist and at least one Dectin-1 agonist for enhancing immune response to a commercial vaccine in a subject wherein the at least TLR4 agonist is selected from monophosphoryl lipid A (MPLA) or glycopyranosyl lipid A (GLA).

[29] Use of at least one TLR7/8 agonist and at least one Mincle agonist for enhancing immune response to a commercial vaccine in a subject.

[30] The use of paragraph 25 or 26, wherein the vaccine composition comprises at least one antigen.

[31] The use of paragraph 30, wherein the at least one antigen is selected from a group consisting of an antigen that is a live attenuated micro-organism that causes known diseases, an antigen that is an inactivated or killed micro-organism that causes known diseases, an antigen that is an inactivated toxin that is produced by a micro-organism that causes known diseases, or an antigen that is a subunit or a conjugate of a subunit of a micro-organism that causes known diseases.

[32] The use of any one of paragraphs 24-31, wherein the at least one TLR7/8 agonist is selected from imidazoquinoline compound R848, gardiquimod, imiquimod, imidazoquinoline compound R848 (resiquimod), CL087, CL097, 3M-052, single stranded RNAs (ssRNAs), 3M-052, benzazepine TLR8 agonist compounds such as VentiRx (VTX)-294, and CL075

[33] The use of any one of paragraphs 24-31, wherein the at least one Mincle agonist is selected from a group consisting of Trehalose-6,6-dibehenate (TDB), *Mycobacterium tuberculosis* (HKMT), Trehalose-6,6-dibehenate formulated with Kolliphor® HS 15 (TDB-HS15), and trehalose-6,6'-dimycolate (TDM).

Those skilled in the art will recognize, or be able to ascertain using not more than routine experimentation, many equivalents to the specific embodiments of the invention described herein. Such equivalents are intended to be encompassed by the following claims.

This invention is further illustrated by the following example which should not be construed as limiting. The contents of all references cited throughout this application, as well as the figures and table are incorporated herein by reference.

EXAMPLE

Due to impairments in cell-mediated immunity, newborns and infants are markedly susceptible to infection with intracellular pathogens. Impaired newborn immunity includes a reduced function of dendritic cells (DCs), key antigen-presenting cells, which puts them at risk for infection and limits their Th1-responses to many vaccines. In this context, there is an unmet need for adjuvants that provide safe but robust stimulation of newborn DCs to produce Th1-polarizing cytokines, resulting in T-cell activation. Our hypothesis was that dual stimulation with Toll-¬like receptor agonists (TLRAs) and C-type lectin agonists (CLRAs) can overcome the reduced response of newborn DCs to common vaccine formulations and thereby enable vaccinations at a younger age.

Adult- and cord blood monocyte-derived DCs (MoDCs) were generated in the presence of autologous plasma, and stimulated with TLRAs and/or CLRAs for 18 hours. The secretion of T-cell polarizing cytokines with PGE2 was measured to assess correlates of immunogenicity and reactogenicity.

Presented data indicate that dual activation through certain TLRs and CLRs can induce enhanced activation of not only adult DCs, but can also enhance newborn DC activation. In adult DCs, dual stimulation through the CLR DNGR-1 together with TLR2, -4 or -8 enhances the production of the T-cell activating and Th1-polarizing cytokines TNF-α, IFN-γ, and the T-helper 17 (Th17)-polarizing cytokine IL-1β. In contrast, in newborn DCs, dual stimulation through the receptors Mincle and TLR8, or through the receptors Dectin-1 and TLR4 is optimal for the induction of Th1-polarizing cytokines. These include the cytokines IFN-γ and IL-12p70, which are important for adaptive immune responses and host defense against intracellular pathogens, and are usually minimally produced by neonatal cells.

These data indicate that targeting vaccinal antigens to the endocytic receptors Mincle or Dectin-1 is a powerful approach to induce Th1-mediated immunity in newborns.

This study shows that combination adjuvants are useful for neonatal vaccines targeting intracellular pathogens, including viral infections, in infants, and result in dramatic public health benefit.

Materials and Methods
TLR Agonists, CLR Agonists, and Assay Reagents

TLR agonists (TLRAs) included Pam3Cys, and Polyinosinic:polycytidylic acid (Poly I:C) (TLR1/2, and TLR3, respectively; INVIVOGEN, San Diego, Calif., USA), ultra-pure lipopolysaccharide (LPS) from *Salmonella minnesota* (TLR4; List Biological Laboratories, Campbell, Calif., USA), MPLA (TLR4; INVIVOGEN™, San Diego, Calif., USA), the imidazoquinolines R848 (TLR 7/8; INVIVOGEN™, San Diego, Calif., USA), VTX-294 (TLR8; VentiRx Pharmaceuticals, Inc., Seattle, Wash.), 3M-052 (TLR8; 3M Pharmaceuticals, St Paul, Minn., USA), and class B CpG oligodeoxynucleotides (CpC ODN) (TLR9; INVIVOGEN™, San Diego, Calif., USA). Glycopyranosyl lipid A (GLA) was courtesy of the Infectious Diseases Research Institute (IDRI). TLRAs were formulated according to manufacturer's recommendations.

CLR agonists (CLRAs) used were Mannan from *Saccharomyces cerevisiae* (DC-SIGN/MMR; SIGMA-ALDRICH Co. LLC., St Louis, Mo., USA), Hepatitis C Virus E2 (HCV E2; DCIR/BDCA-2; eENZYME LLC, Gaithersburg, Md., USA), and biotin glycoprotein 120 (gp120; BDCA-2/DC-SIGN; Immunodiagnostics, Inc., Woburn, Mass., USA). Zymosan (alkaline-treated; Dectin-1), Curdlan (DNGR-1), Trehalose-6,6-dibehenate (TDB; Mincle), β-glucan peptide (BGP) (Dectin-1) and Whole Glucan Particles (WGP) were all purchased from the same supplier (INVIVOGEN™, San Diego, Calif., USA). CLRAs were formulated according to manufacturer's recommendations.

All TLRAs (other than LPS and MPLA) and CLRAs were verified to be free of endotoxin (<1 EU/ml), as measured by Limulus amoebocyte lysate (LAL) assay per protocol provided by manufacturer (Charles River, Wilmington, Mass., USA)1.

Sterile Dulbecco's Phosphate Buffered Saline (DPBS) without $Ca^{2+}$, $Mg^{2+}$, and Phenol Red (GIBCO®—Life Technologies, Carlsbad, Calif., USA) was included in several assays as a negative control.

Blood Samples

Non-identifiable cord blood samples were taken with approval from the Ethics Committee of The Beth Israel Deaconess Medical Center, Boston, Mass. (protocol number 2011P-000118). All de-identified blood samples from adult and elderly subjects included in the experiments provided written informed consent with approval from the Ethics Committee of Boston Children's Hospital, Boston, Mass. (protocol number X07-05-0223). All de-identified blood samples from infant subjects included in the experiments provided written informed consent from the parents with approval from the Ethics Committee of Boston Children's Hospital, Boston, Mass. (protocol number P00010750).

Peripheral blood was collected from healthy adult volunteers (2) (approximately 200 ml), and umbilical cord blood from full-term newborns (approximately 30-60 ml) was collected immediately after cesarean section delivery of the placenta (HIV-positive mothers and mothers presenting with fever during delivery were excluded).

Blood samples were processed within 4 hours (typically within 1-2 hours), and anticoagulated with 15 U/ml pyrogen-free heparin sodium (American Pharmaceutical Partners, Inc., Schaumberg, Ill., USA). The number of study subjects (n) used for each experimental approach is presented in the figure legends. Human experimentations guidelines of the US Department of Health and Human Services, Beth Israel Deaconess Medical Center, Brigham and Women's Hospital, and Boston Children's Hospital were observed, according to approved local Institutional Review Board protocols.

Isolation of Mononuclear Cells and Monocytes

Heparinized blood from adults and newborns was centrifuged for 10 minutes at 0.5 Relative Centrifugal Force (RCF), after which the upper layer of clear yellow plasma was removed. This platelet-rich plasma (PRP) was then centrifuged for 15 minutes at 3000 RCF, and platelet-poor plasma (PPP) was collected from the top and stored at −20° C. The remaining blood was reconstituted to its original volume by resuspending in DPBS (GIBCO®—Life Technologies, Carlsbad, Calif., USA). Then, 25 ml of reconstituted blood was layered onto 15 ml of Ficoll-Hypaque gradients (Ficoll-Paque PREMIUM®, GE Healthcare, Waukesha, Wis., USA) and centrifuged for 30 minutes at 0.5 RCF. After Ficoll separation centrifugation the PBMC or CBMC layer (buffy coat) was collected.

Monocytes were then isolated from mononuclear cell fractions by positive selection with magnetic CD14 Micro-Beads, performed according to manufacturer's instructions (Miltenyi Biotec, Auburn, Calif., USA).

Blood Assay

For assessment of TLRA activity in whole blood, we used an adaptation of a previously described method. Neonatal cord blood or infant peripheral blood or adult peripheral blood was mixed 1:5 with sterile pre-warmed (37° C.) RPMI 1640 medium (Invitrogen; Carlsbad, Calif., USA) and 135 mL of the 1:1 suspension was added to each well of a 96 well U-bottom plate (Becton Dickinson; Franklin Lakes, N.J., USA) containing 15 µl freshly prepared agonists at 10× the final concentration. Suspensions containing 150 µl/well were gently mixed by pipetting and incubated for 24 h at 37° C. in a humidified incubator at 5% $CO_2$. After culture, plates were centrifuged at 500×g and supernatant was carefully removed by pipetting without disturbing the cell pellet. Supernatants derived from human leukocyte stimulations were assayed by ELISA for TNFα (BD Biosciences; San Jose, Calif., USA). The minimum threshold for each analyte was set at the minimum detectable dose for that particular assay (defined as three standard deviations above the mean background).

Generation and Maturation of MoDCs with GM-CSF and IL-4

Isolated monocytes were seeded in 75 $cm^2$ tissue culture dishes for 5 days at 37° C. in a humidified incubator at 5% $CO_2$ with $10^6$ cells/ml medium. Medium consisted of RPMI 1640 medium with L-glutamine (GIBCO—LIFE TECHNOLOGIES, Carlsbad, Calif., USA) supplemented with 1% Penicillin-Streptomycin-Glutamine (PSG) (Invitrogen—Life Technologies, Carlsbad, Calif., USA) and 10% AP. This was supplemented with recombinant human (rh) IL-4 and rhGM-CSF (50 ng/ml and 100 ng/ml, respectively; R&D Systems, Minneapolis, Minn., USA). Additional fresh media and cytokines were provided on day 3 of incubation.

After 5 days, immature MoDCs were harvested by gently pipetting only the loosely adherent fraction and re-plated ($10^5$ cells/well) in 96-well U-bottom plates in the presence or absence of TLRAs, and/or CLRAs, and/or sterile DPBS. This MoDC array was then incubated for 18-24 hours at 37° C. in a humidified incubator at 5% $CO_2$. After this stimulation MoDCs were harvested and processed for further functional assays. (FIG. 2).

Gene Expression Analysis by Quantitative RT-PCR Array

Total ribonucleic acid (RNA) of newborn and adult MoDCs (GCI-DCs and TC-DCs) was isolated with the miRNeasy kit, according to manufacturer's instructions (QIAGEN®, Inc., Valencia, Calif., USA) Total RNA from both un-stimulated cells and cells stimulated with 1 µg/ml MPLA was isolated. RNA quality was analyzed for quality and quantity by using a NanoDrop 1000 spectrophotometer (Thermo Scientific, Wilmington, Del., USA). Complementary deoxyribonucleic acid (cDNA) was prepared from total RNA from each sample with a miScript II RT Kit, according to manufacturer's instructions (QIAGEN®, Inc., Valencia, Calif., USA). cDNA was quantified on a PAHS-052Z plate (QIAGEN®, Inc., Valencia, Calif., USA). Quantitative real time-polymerase chain reaction (RT-PCR) was run on a 7300 real time PCR system (APPLIED BIOSYSTEMS®—Life Technologies, Life Technologies, Carlsbad, Calif., USA).

TNF-Alpha Measurement by ELISA

Supernatants from MoDCs (GCI-DCs) stimulated for 18 hours in a humidified incubator (37° C., 5% $CO_2$) with TLRAs, and/or CLRAs were analyzed for TNF-α production. For this, a human TNF enzyme-linked immunosorbent assay (ELISA) kit was used, and assay was performed according to manufacturer's instruction. (BD Biosciences, BD Biosciences, San Jose, Calif., USA). Results were read on a Versamax microplate reader with SoftMax Pro Version 5 (both from Molecular Devices, Sunnyville, Calif., USA).

Cytokine Measurement by Multi-Analyte Fluorescent Bead-Based Array

Cytokine profile of both un-stimulated MoDCs (GCI-DCs and TC-DCs), and MoDCs stimulated for 18 hours with TLRAs and/or CLRAs was analyzed using multi-analyte bead array (Milliplex). Cytokines were quantified from culture supernatants with the Cytokine Human Magnetic 30-Plex Panel from INVITROGEN™—Life Technologies (Carlsbad, Calif., USA), or a custom-designed array, including IFN-alpha2, IFN-gamma, IL-10, IL-12p40, IL-12p70, IL-1b, IL-6, and TNF-alpha Results were obtained with a MAGPIX system with xPONENT software (both from LUMINEX Corp., Austin, Tex., USA).

Flow Cytometry

After stimulation of moDCs and removal of culture supernatants for subsequent analysis, cell pellets were resuspended in PBS/0.5% Human Serum Albumin (HSA, Octapharma USA, Inc., Hoboken, N.J., USA) and stained with any of the following fluorescent antibodies: anti-CD14-V450 (clone MφP9), anti-HLA-DR-PE.Cy7 (clone G46-6), anti-CD80-PE.Cy7 (clone L307.4), anti-CD83-APC (clone HB15c) and anti-CD209-V450 (clone DCN46) were purchased from BD Biosciences (San Jose, Calif., USA), anti-TLR4-FITC (clone 76B357.1) was purchased from Thermo Scientific (Wilmington, Del., USA). Anti-Dectin-1-APC (clone 259931) was purchased from R&D Systems (Minneapolis, Minn., USA). Anti-Mincle antibody (clone 15H5) was purchased from Invivogen (San Diego, Calif., USA) and labeled using an AlexaFluor® 488 labeling kit (LIFE TECHNOLOGIES).

For detection of intracellular TLR7 or TLR8, cells were Fixated with 3.7% paraformaldehyde and permeabilized with BD Fix/Perm (BD BIOSCIENCES) before staining with anti-TLR7-PE (clone 4G6) or anti-TLR8-PE (clone 44C143) (Thermo Scientific (Wilmington, Del., USA). Cells were analyzed on an LSRFortessa flow cytometer (BECKTON DICKINSON) and analyzed with Flowjo software version 10 (TREE STAR, Inc.; Ashland, Oreg., USA).

Naïve T-Cell Stimulation

Naive CD4+ T cells were purified using negative-selection beads (Miltenyi Biotec; Auburn, Calif., USA). Isolated naïve T cells were cultured for 6 days in 96-well plates at a density of $8 \times 10^4$ cells per well in 100% conditioned media from moDC cultures which were stimulated as indicated, in the presence of CD3/CD28 T Cell Expander Dynabeads (one bead per cell; LIFE TECHNOLOGIES,). As a positive control for Th1-polarization, cells were cultured in the presence of 10 ng/ml IL-12 instead of MoDC-conditioned media. On day 6, beads were removed and replaced with fresh beads. Cells producing IFN-γ, IL-4, IL-10 or IL-17 were analyzed by intracellular cytokine staining after the addition of BD Golgiplug (BD BIOSCIENCES) during the final 6 h of restimulation. Cells were made permeable with Cytofix/Cytoperm reagents (BD BIOSCIENCES). Cells were stained with anti-IFN-γ-PE.Cy7 (clone B27, BD Biosciences), anti-IL-17-APC (clone 41802, R&D Systems), anti-IL-4-V450 (clone 8D4-8, BD Biosciences) and anti-IL-10-AlexaFluor® 488 (clone JES3-9D7, Biolegend). Cells were analyzed for production of these four cytokines by flow cytometry on an LSRFortessa flow cytometer (BECKTON DICKINSON) and analyzed with FLOWJO software version 10 (TREE STAR, Inc).

Caspase-1 Activity Measurement

Figure 3:
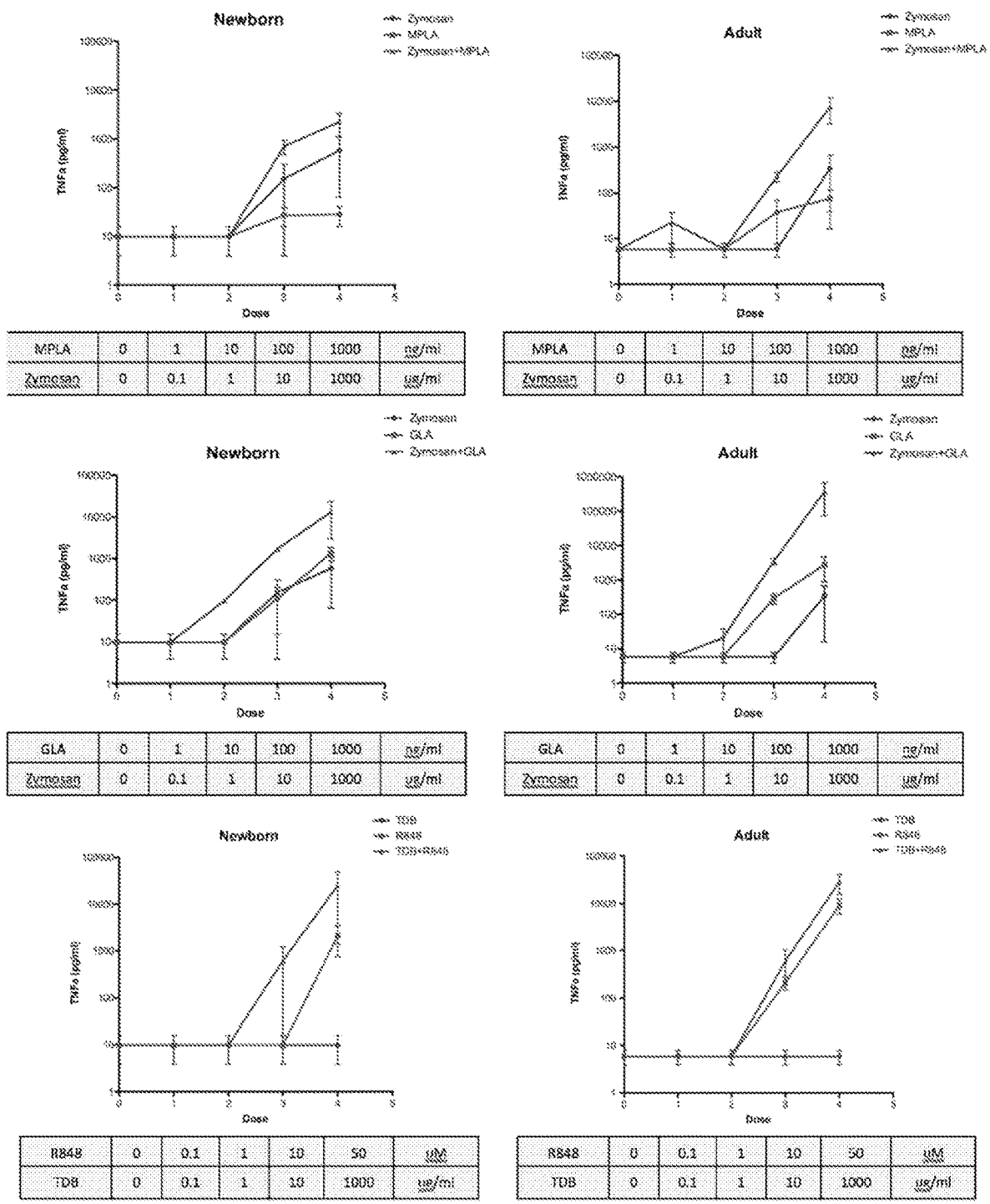
FIG. 3 shows that TLRAs and CLRAs synergistically induce MoDC TNF production. Adult and newborn MoDCs were stimulated with TLRAs, CLRAs, or combination as indicated. Secreted TNF-α was measured by ELISA. Alkali-treated Zymosan (Dectin-1A) has the ability to synergize with both TLR4As (MPLA and GLA) to induce TNF-α production by newborn moDCs.

Newborn MoDCs were generated as described above and stimulated with individual or combined agonists as indicated in FIG. 3, at $5 \times 10^5$ cells per condition for 6 hours at 37° C. During the last hour of the incubation, a fluorescent Caspase-1 inhibitor, FAM-YVAD-FMK (SEQ ID NO: 1) (ImmunoChemistry Technologies, LLC; Bloomington, Minn., U.S.A.) was added to detect activated Caspase-1. Cells were subsequently fixed in 4% PFA and fluorescent intensity at 488 nm was measured by flow cytometry on an LSRFortessa flow cytometer (Beckton Dickinson, San Jose, Calif., USA) and analyzed with Flowjo software version 10 (TREE STAR, Inc., Ashland, Oreg, USA).

Western Blotting

Newborn moDCs were generated as described above and stimulated with individual or combined agonists as indicated in FIG. 3, at $5 \times 10^5$ cells per condition for 30 minutes at 37° C. Cells were lysed in RIPA buffer containing 1% protease inhibitors (SIGMA-ALDRICH Co. LLC.; St Louis, Mo., USA). Protein concentration in cell lysates was determined using a BCA protein determination kit (LIFE TECHNOLOGIES) and 25 µg of each sample was run on a 10% Bis-Tris protein gel (LIFE TECHNOLOGIES) and transferred to a nitrocellulose membrane. IκBα and GAPDH were detected using mouse monoclonal antibodies (clone L35A5, Cell Signaling, Danver, Mass., USA and clone 6C5, ABCAM, Cambridge, Mass., USA) and HRP-linked anti-mouse IgG (CELL SIGNALING, Danver, Mass., USA).

Results

To evaluate the ability of TLRAs to activate human newborn and adult MoDCs, the inventors measure the effect of treatment with MPLA (TLR4A) on expression of 84 genes of the innate immune system (FIG. 1). These data show that newborn MoDCs produce more IL-6 and IL-10 than adult MoDCs. In contrast, adult MoDCs have higher expression levels of IRF7 and IRAK1, both important transducers of TLR signals to the secretion of Th1-inducing cytokines. The TNF gene was also expressed 2-fold higher in the adults, as compared to newborns. The previous observations have confirmed that newborns produce less TNF-α in response to TLR4 stimulation than adults. (7)

To assess whether combinations of PRRAs may overcome the reduced production of TNF-α and the reduced ability to induce Th1-mediated immunity, we screened different combinations of TLRAs and CLRAs for the ability to induce adult-like levels of TNF-α secretion from newborn MoDCs (FIG. 2).

The screen indicates that newborn MoDCs produced robust, adult-like levels of TNF-α after stimulation with either MPLA+Zymosan (TLR4+Dectin-1 activation) or after stimulation with R848+TDB (TLR7/8+Mincle activation). In FIG. 3 the inventors show dose-response curves of these particular combinations. In addition, the Dectin-1A (Zymosan) also displays a similar synergy in combination with another TLR4A, glycopyranosyl lipid A (GLA), a synthetic LPS congener currently in human clinical trials. (8)

Figure 4:
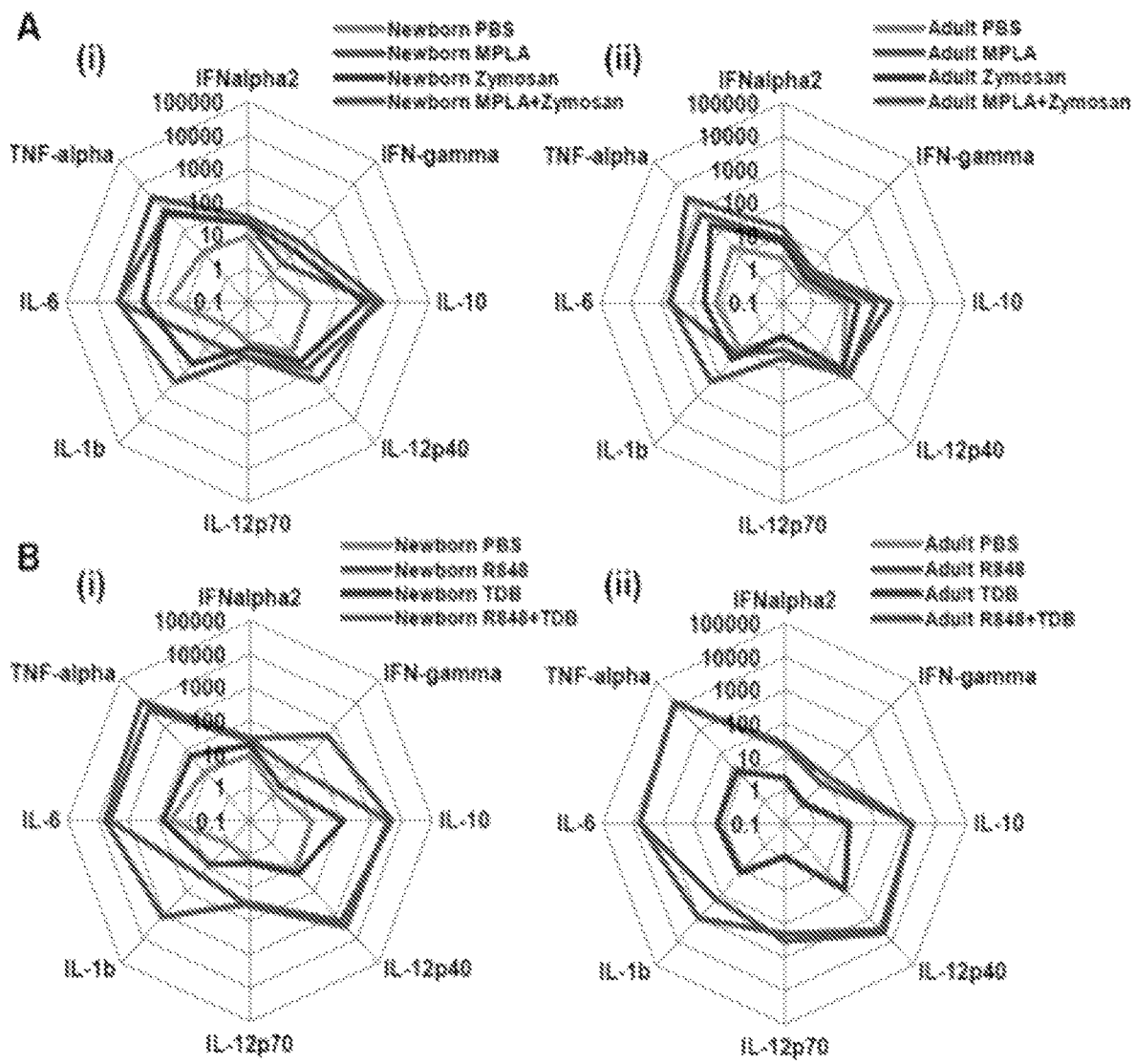
FIGS. 4A and 4B show that dual synergistic stimulation with CLRAs and TLRAs induces robust synergistic secretion of T-cell polarizing cytokines. Newborn and adult MoDCs were generated in the presence of 10% autologous plasma and incubated for 18 hours with (combinations of) indicated TLRAs and CLRAs. Supernatants were collected and cytokine profile was analyzed by multi-analyte fluorescent bead array (N=3).
Figure 5:
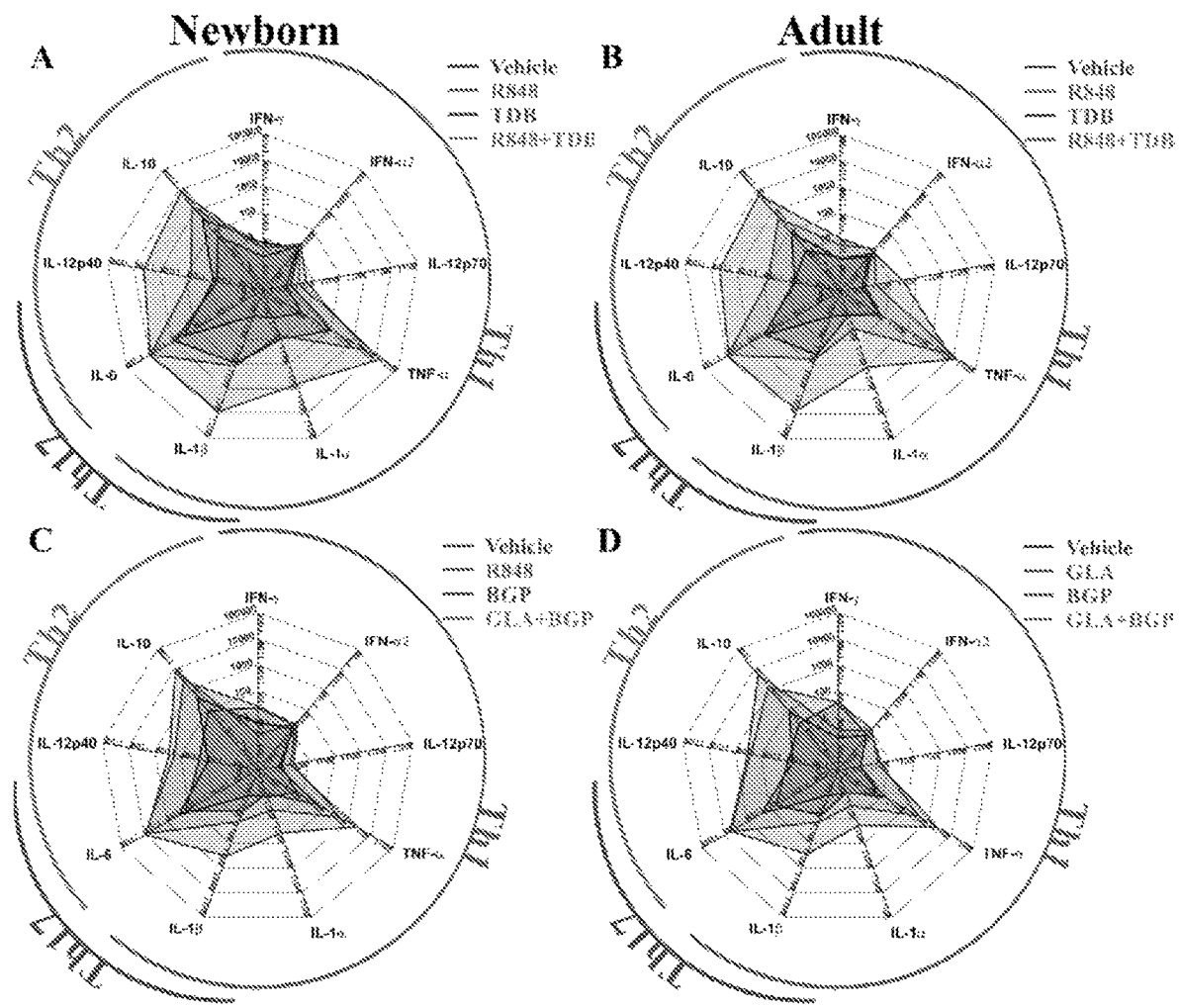
FIG. 5 shows that synergistic stimulation with CLRAs and TLRAs induces robust synergistic secretion of T-cell polarizing cytokines. Newborn and adult MoDCs were generated in the presence of 10% autologous plasma and incubated for 18 hours with (combinations of) indicated TLRAs and CLRA—with TDB, R848 or both (A+B) and with zymosan, MPLA or both (C+D). Supernatants were collected and cytokine profile was analyzed by multi-analyte fluorescent bead array (N=3). Adult and newborn DCs were generated in the presence of 10% autologous plasma (AP) and (N=3) Both combinations of TLRA and CLRA restore the production of TNF to adult-like levels. In addition, both combinations induce the secretion of IL-1β and IFN-γ, which may restore T-cell polarization to Th1 and Th17 subsets (A+C). Synergistic stimulation the production of Th1-polarizing TNF-α, IL-1α and IL-1β, while reducing the production of Th2-polarizing IL-12p40 and IL-10.
Figure 6:
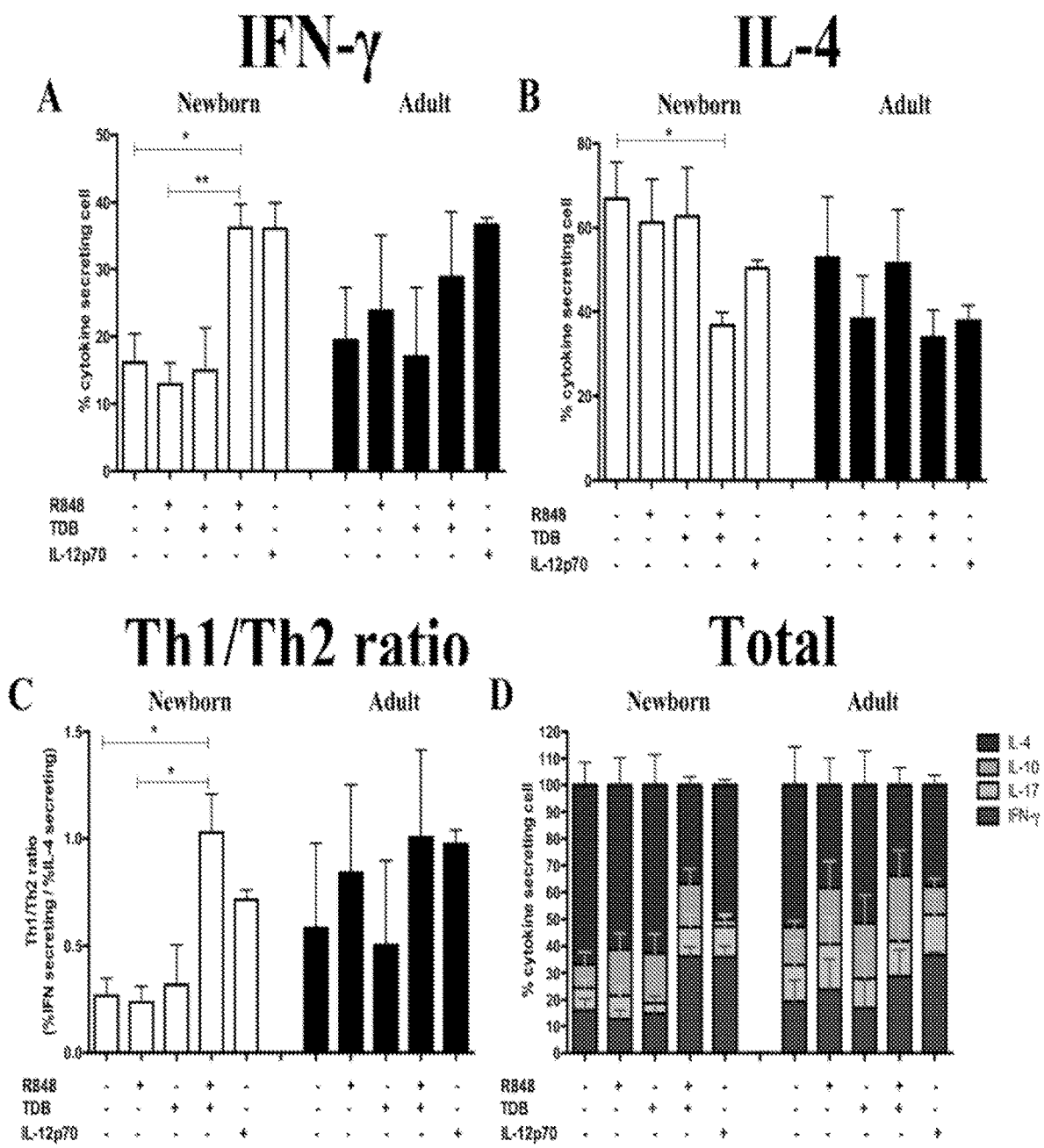
Figure 6:
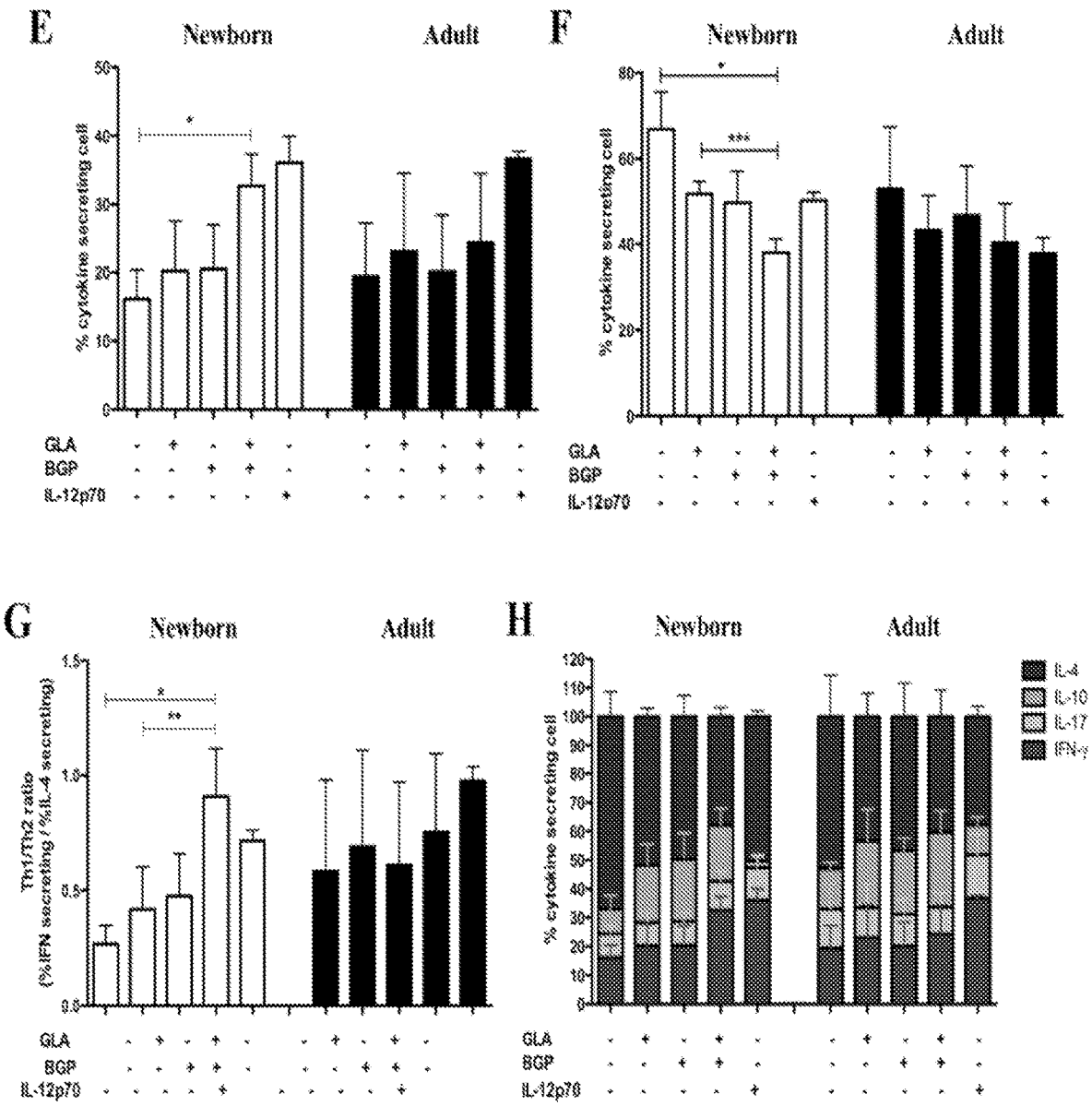

In addition to inducing elevated, adult-like levels of TNF-α, the inventors investigated whether these combinations of stimuli have driven newborn MoDCs to secrete Th1-inducing cytokines (FIG. 4). Indeed, both combinations of stimuli induce the secretion of IFN-γ and IL-1β.

Overall, dual stimulation of newborn MoDCs with TLR4A (e.g., MPLA or GLA) and a Dectin-1A (e.g., Zymosan) or with a TLR7/8A (e.g., R848) and a MincleA (e.g., TDB) induces adult-like levels of Th1 (TNF-α, IFN-γ) and Th17 (IL-1β)-polarizing cytokines. Accordingly, these TLRA/CLRA combinations may represent novel adjuvantation systems to enable early life inmmunization against intracellular pathogens. In addition, CLRs are endocytic receptors. Targeting vaccine antigens to a CLR could therefore also assist in internalization of vaccine antigens by DCs, which can further enhance vaccine efficacy.

Previously published observations from our lab and others have established that an important aspect of the functionally distinct immune system of newborns is the diminished production of TNF-α by monocytes and DCs in response to TLR4 stimulation, as compared to adults. This was confirmed by stimulation of adult and newborn moDCs with TLR agonists. FIG. 2 shows that newborn MoDCs produce less TNF in response to Pam3Cys (TLR2), Poly I:C (TLR3), MPLA (TLR4) LPS (TLR4) and R848 (TLR7/8). Interestingly, TNF-α secretion in response to CLR agonists is in many cases also impaired, except for the Dectin-1 agonists alkali-treated Zymosan and whole glucan particles (WGP). To evaluate what could cause the impaired response to TLRAs in newborn MoDCs, we measured the expression of 84 genes of the innate immune system before and after treatment with MPLA (FIG. 1). These data show that after treatment with MPLA the IL6 and CXCL-8 (IL8) genes are expressed greater in newborn MoDCs than in adult MoDCs. In contrast, adult MoDCs demonstrate greater expression of IRF7, IRAK1 and NFKB1, important transducers of TLR signals to the secretion of Th1-inducing cytokines. These observations suggested that NF-κb activation following TLR activation may be impaired in newborn moDCs. Some CLRs have the ability to activate NF-κb in a IRAK1-independent fashion. To assess whether combinations of CLRAs and TLRAs may overcome the reduced production of TNF and the reduced ability to induce Th1-mediated immunity, different combinations of TLRAs and CLRAs we screened for induce adult-like levels of TNF-α secretion from newborn MoDCs (FIG. 2).

Figure 2A:
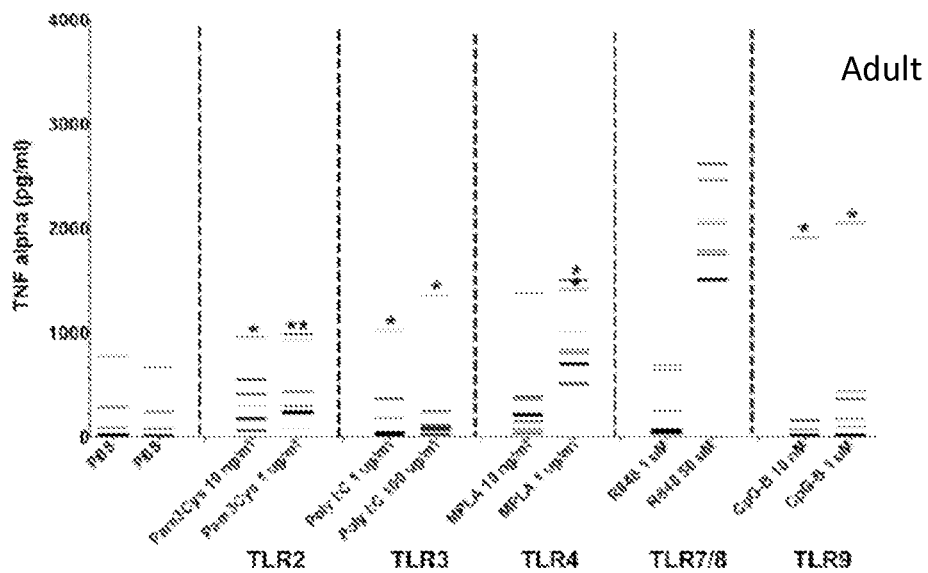
FIGS. 2A-2F show that TLRAs and CLRAs synergistically induce TNF production by Human newborn and adult MoDCs. Newborn and adult MoDCs were generated in the presence of 10% autologous plasma and incubated for 18 hours with combinations of indicated TLRAs and CLRAs. Supernatants were collected and analyzed by TNF-α ELISA (n=3).
Figure 2B:
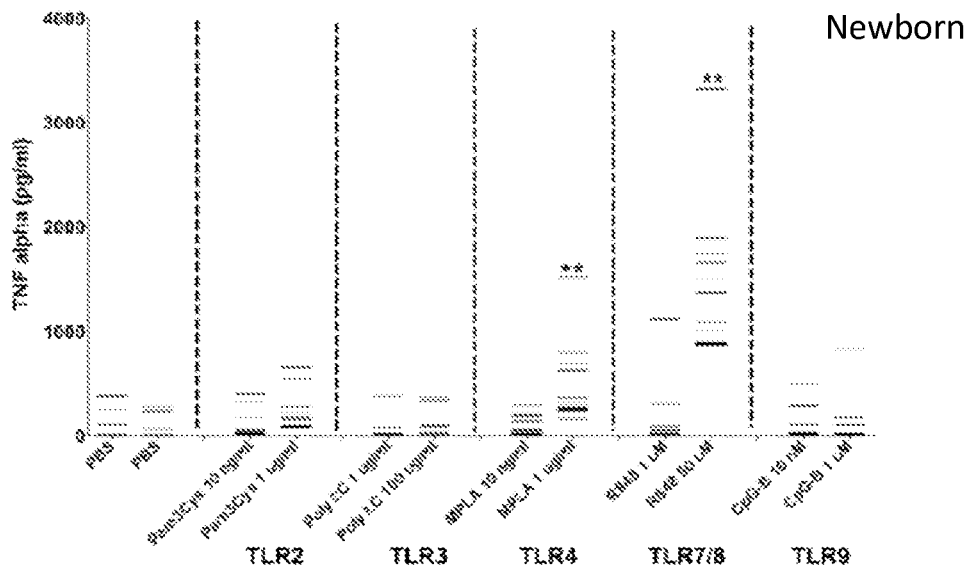
Figure 2C:
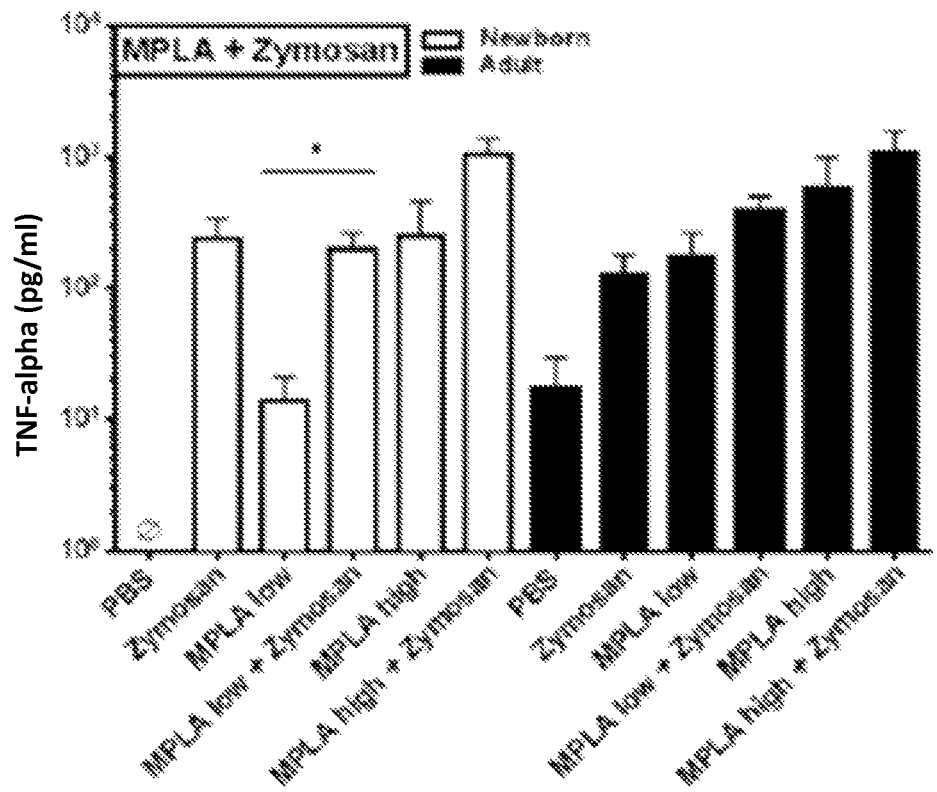
Figure 2D:
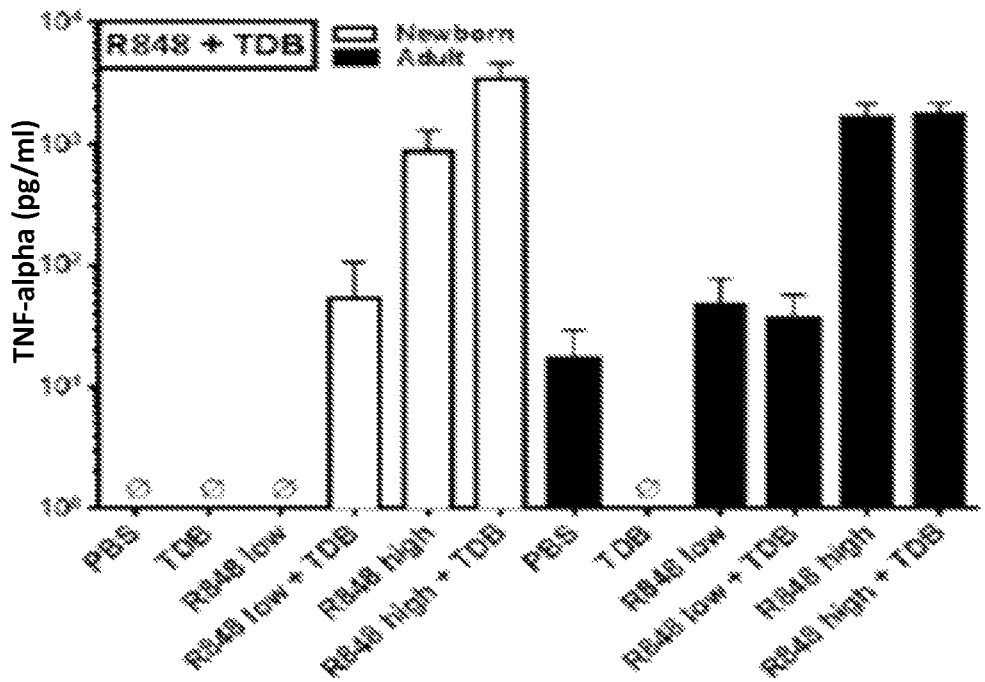
Figure 2E:
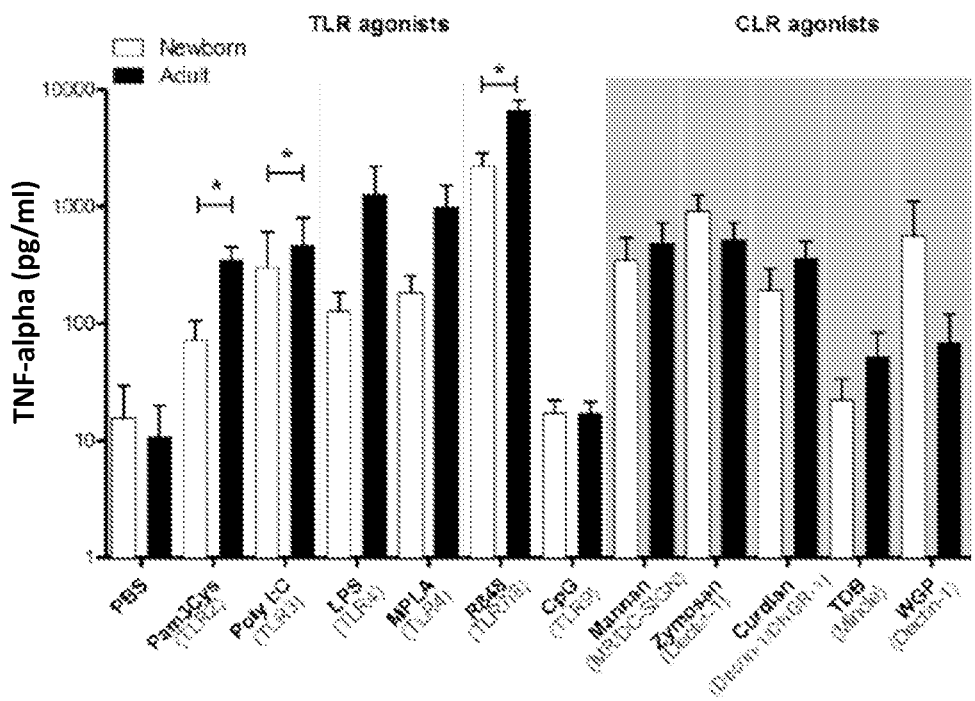
Figure 2F:
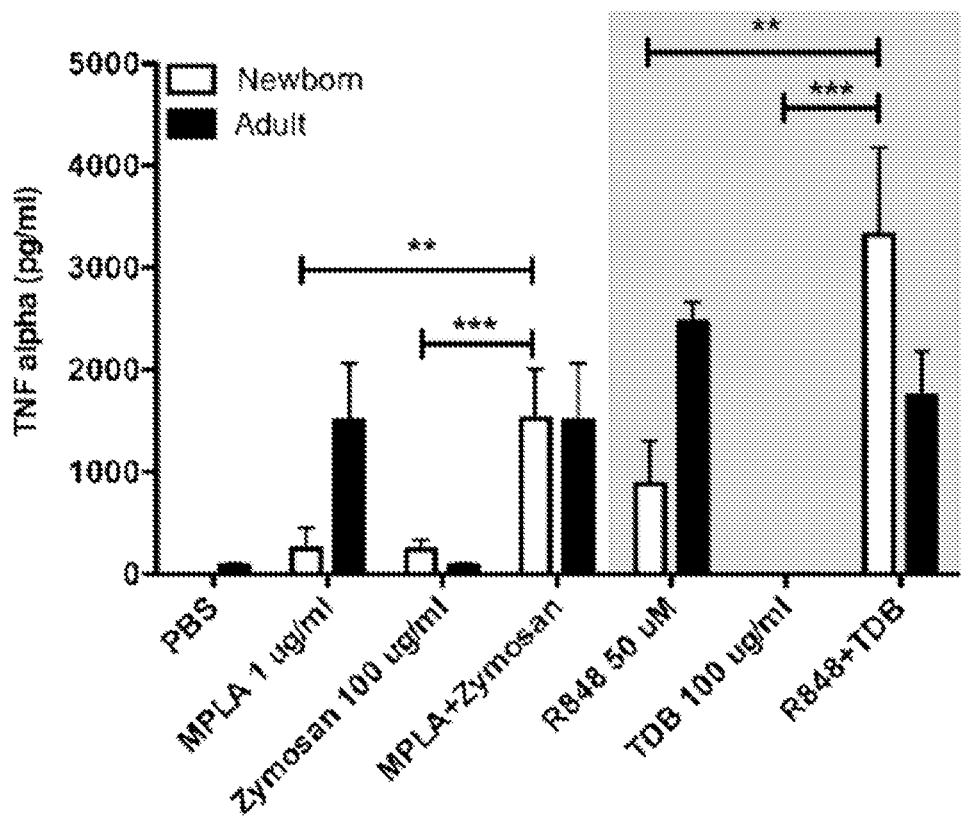

The screen indicated that adult MoDCs demonstrated enhanced TNF production after combined stimulation with alkali-treated zymosan (Dectin-1) and Pam3Cys (TLR2) or MPLA (TLR4), as compared to stimulation with each of the agonists individually. In addition, combined stimulation with Mannan (Mannose Receptor) and CpG (TLR9; FIG. 2A) resulted in a similar elevation. Stimulation of newborn MoDCs with TLRAs resulted in lower levels of TNF production compared to adult MoDCs (FIG. 2A). Two combinations of agonists induced increased TNF secretion: 1) Stimulation with Zymosan and MPLA resulted in elevated, adult-like TNF secretion, whereas 2) stimulation with TDB (Mincle) and R848 (TLR7/8) induced even higher amounts of TNF-α, not observed with any other combination, even in adult moDCs. TNF production following activation with both these combinations was significantly higher than with each of the individual agonists (FIGS. 2C-2F).

The inventors further evaluated the ability of these two combinations of agonists to activate newborn MoDCs by establishing concentration-response curves and by investigating whether the enhancement in TNF secretion can be observed with similar agonists that activate the same receptors. In addition, the concentration-response curves were used to mathematically assess whether the observed enhancement by combining agonists is equal to the sum of the effects observed with individual agonists (i.e., was additive) or if these agonists activate the newborn cells synergistically. A modification of the Loewe definition of additivity was applied to determine whether the agonists act synergistically (D<1), additively (D=1) or antagonistically (D>1), where D=[Ac]/[Ae]+[Bc]/[Be], and [Ac] and [Bc] are the concentrations of compound A and B used in the dual (combined) stimulation and [Ae] and [Be] are the concentrations of A and B that induce an equal amount of TNF secretion alone.

FIG. 3 confirms that synergistic enhancement of TNF production induced by TDB+R848 was most prominent in newborn cells (FIG. 3, D=0.1332 vs 0.6877 in adults), as this combination did not indicate synergy in adults during the screen. A similar effect is observed when R848 (TLR7/8) is substituted for VTX-294 (TLR8), indicating that synergy was not compound-specific effect, but rather a general effect of stimulation through Mincle and TLR8 (FIG. 3). The combination of MPLA+Zymosan (FIG. 3) acts in a synergistic fashion in both newborns and adults. Similarly, the observed synergy between MPLA and Zymosan is also present when glycopyranosyl lipid A (GLA), a synthetic LPS congener currently in human clinical trials, is used instead of MPLA and when β-glucan peptide (BGP), another Dectin-1 agonist, is used instead of alkali-treated Zymosan. Overall, these observations suggest a common synergistic effect when stimulating newborn MoDCs through TLR4 and Dectin-1.

The effects of synergistic TLRA/CLRA combinations were further characterized, by measuring gene expression analysis of a select panel of 80 genes, associated with several innate immune activation pathways. 8 genes are upregulated more than 3-fold (p<0.05) when newborn moDCs are treated with R848+TDB (Data not shown). Treatment with GLA+BGP enahnced expression of 7 of the 80 genes measured. The treatment of newborn moDCs with either R848+TDB or GLA+BGP increased the expression of NF-κB- and NLRP3 inflammsome-associated genes, as compared with treatment with either of the agonists alone. Because changes in pathway-associated gene expression do not necessarily correspond with actual activation of that pathway, we investigated whether synergistic activation of newborn MoDCs coincides with inflammasome activation and increased NF-κB activation, by measuring activation of Caspase-1 and degradation of IκB, respectively. TLRAs induced moderate Caspase-1 activation and moderate IκB degradation whereas both the CLRAs induced more substantial Caspase-1 activation but less IκB degradation. Only when treated with either of the TLRA/CLRA combinations, R848+TDB or GLA+BGP, was robust Caspase-1 activation as well as near complete IκB degradation observed.

In addition to inducing elevated, adult-like levels of TNF, we investigated whether these combinations of stimuli can drive newborn MoDCs to secrete Th1-inducing cytokines. FIG. 4 confirm that synergistic stimulation with R848+TDB induces similar, robust levels of TNF in newborn and adult MoDCs. In comparison to stimulation with R848 alone, a strong decrease in the production of Th2/Treg cytokines IL-12p40 and IL-10 was noted, coinciding with an increase in Th1/17 cytokines IL-1β and IL-1α. Similarly, synergistic stimulation with GLA+BGP decreased IL-10 and IL-12p40 production, as compared to stimulation with GLA alone, and production of IL-1β and IL-1α. Synergistic production of IL-1β protein was in line with the gene expression and caspase-1 activation results.

In order to evaluate the effect of this complex network of MoDC-derived signals and cytokines on actual T-cell proliferation, we stimulated naïve CD4+ T cells with CD3/CD28 beads in the presence of culture supernatants from CLRA/TLRA-stimulated autologous MoDCs. The cytokines secreted by newborn MoDCs after dual stimulation with TDB+R848 or with GLA+BGP were significantly reduced Th2-polarization and increased the polarization of naïve T cells to Th1 cells, as measured by intracellular staining for the cytokines IFN-γ, IL-4, IL-10 and IL-17.

The ability of the select TLRA/CLRA combinations R848+TDB or GLA+BGP to activate primary leukocytes in blood and across additional age groups was determined using a whole-blood assay. Cord blood (newborn) and peripheral blood from infants (~6 months) and adults (18-40 years) was diluted in RPMI and directly stimulated with agonists as indicated in FIG. 3. Analysis of TNF secretion in culture supernatants indicates synergistic activation at different concentrations of agonists in newborns, infants and adults for Zymosan+GLA, and for newborns and infants, but not adults, for TDB+R848.

Analysis of MoDC cell surface receptors after individual or combined dual stimulation with TLRAs and CLRAs reveals that dual activation with either R848+TDB or with GLA+BGP induces the surface expression of T-cell stimulatory molecules HLA-DR, CD80 and CD83 to a similar extent as stimulation with any of the single agonists (Data not shown). There was, however, a notable difference in the expression of the receptors that the cells were activated through. When compared to stimulation with individual agents, whereas stimulation with GLA+BGP increased expression of Dectin-1, stimulation with TDB+R848 increased expression of TLR8.

The references cited herein and throughout the specification are incorporated herein by reference.

REFERENCES

1. Levy, O. 2007. Innate immunity of the newborn: basic mechanisms and clinical correlates. Nat Rev Immunol 7: 379-390.
2. Kollmann, T. R., O. Levy, R. R. Montgomery, and S. Goriely. 2012. Innate Immune Function by Toll-like Receptors: Distinct Responses in Newborns and the Elderly. Immunity 37: 771-783.
3. Cambi, A., and C. G. Figdor. 2003. Dual function of C-type lectin-like receptors in the immune system. Curr Opin Cell Biol 15: 539-546.
4. Eberle, M. E., and A. H. Dalpke. 2012. Dectin-1 Stimulation Induces Suppressor of Cytokine Signaling 1, Thereby Modulating TLR Signaling and T Cell Responses. Journal of immunology.
5. Geijtenbeek, T. B., and S. I. Gringhuis. 2009. Signalling through C-type lectin receptors: shaping immune responses. Nature reviews. Immunology 9: 465-479.
6. Kingeter, L. M., and X. Lin. 2012. C-type lectin receptor-induced NF-kappaB activation in innate immune and inflammatory responses. Cellular & molecular immunology 9: 105-112.
7. Levy, O., K. A. Zaremberg, R. M. Roy, C. Cywes, P. J. Godowski, and M. R. Wessels. 2004. Selective impairment of TLR-mediated innate immunity in human newborns: neonatal blood plasma reduces monocyte TNF-alpha induction by bacterial lipopeptides, lipopolysaccharide, and imiquimod, but preserves the response to R-848. Journal of immunology 173: 4627-4634.
8. Lambert, S. L., C. F. Yang, Z. Liu, R. Sweetwood, J. Zhao, L. Cheng, H. Jin, and J. Woo. 2012. Molecular and Cellular Response Profiles Induced by the TLR4 Agonist-Based Adjuvant Glucopyranosyl Lipid A. PloS one 7: e51618.
9. Gantner B. N. et al., 2003. Collaborative induction of inflammatory responses by dectin-1 and Toll-like receptor 2. J Exp Med. 197:1107-17
10. Dennehy K. M. et al., 2008. Syk kinase is required for collaborative cytokine production induced through Dectin-1 and Toll-like receptors. Eur. J. Immunol. 38: 500-506
11. Lee W B et al. 2012. Neutrophils Promote Mycobacterial Trehalose Dimycolate-Induced Lung Inflammation via the Mincle Pathway. PLOS Pathogen. 8: e1002614.
12. Maria da Glo'ria Sousa et al. 2011. Restoration of Pattern Recognition Receptor Costimulation to Treat Chromoblastomycosis, a Chronic Fungal Infection of the Skin. Cell Host & Microbe 9, 436-443.

What is claimed is:

1. A synergistic composition comprising at least one TLR7/8 agonist, at least one Mincle agonist, and at least one antigen, and is formulated as a vaccine composition, wherein the composition activates newborn monocyte-derived dendritic cells (MoDCs) in an amount higher than a sum of activation of newborn MoDCs by the TLR7/8 agonist and the Mincle agonist used alone.

2. The composition of claim 1, the composition further comprising at least one TLR4 agonist and at least one Dectin-1 agonist, wherein the at least TLR4 agonist is selected from monophosphoryl lipid A (MPLA) or glycopyranosyl lipid A (GLA).

3. The composition of claim 1, wherein the at least one TLR7/8 agonist is selected from the group consisting of gardiquimod, imiquimod, imidazoquinoline compound R848 (resiquimod), CL087, CL097, and CL075.

4. The composition of claim 1, wherein the at least one Mincle agonist is selected from a group consisting of Trehalose-6,6-dibehenate (TDB), HKMT, TDB-HS15, and TDM.

5. A method of enhancing an immune response to an antigen in a subject comprising administering a composition of claim 1 to the subject.

6. The composition of claim 1, wherein the at least one antigen is selected from a group consisting of an antigen that is a live attenuated micro-organism that causes known diseases, an antigen that is an inactivated or killed micro-organism that causes known diseases, an antigen that is an inactivated toxin that is produced by a micro-organism that causes known diseases, or an antigen that is a subunit or a conjugate of a subunit of a micro-organism that causes known diseases.

7. The composition of claim 1, wherein the combination of the at least one TLR7/8 agonist and at least one Mincle agonist is in an amount of about 85 to 99% of the mass of the vaccine.

8. The composition of claim 1, wherein the at least TLR7/8 agonist is in the range of about 0.1 to about 5% of the mass of the fraction.

9. The composition of claim 1, wherein the at least Mincle agonist is in the range of about 0.1 to about 5% of the mass of the fraction.

10. The composition of claim 1 further comprising alum-hydroxide as a co-adjuvant.

11. The composition of claim 1, wherein the combination of the at least one TLR7/8 agonist and at least one Mincle agonist in the composition is about 150 µg to 150 mg/single dose.

12. The composition of claim 1, wherein the vaccine is formulated in an oil-in-water emulsion.

13. The composition of claim 1, wherein the Mincle agonist is present in an amount that is insufficient to activate monocyte-derived dendritic cells when the Mincle agonist is used alone.

14. The composition of claim 1, wherein the at least one TLR7/8 agonist is resiquimod and the at least one Mincle agonist is TDB.

15. The composition of claim 8, wherein the vaccine composition is formulated as an oral or injectable solution.

16. The composition of claim 9, wherein the vaccine composition is formulated as an oral or injectable solution.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Val Ala Asp
1